US008163487B2

(12) United States Patent
Gelfand et al.

(10) Patent No.: US 8,163,487 B2
(45) Date of Patent: Apr. 24, 2012

(54) 2'-TERMINATOR NUCLEOTIDE-RELATED METHODS AND SYSTEMS

(75) Inventors: David Harrow Gelfand, Oakland, CA (US); Fred Lawrence Reichert, San Leandro, CA (US); Veeraiah Bodepudi, San Ramon, CA (US); Amar Gupta, Danville, CA (US); Stephen Will, Cham (CH); Thomas W. Myers, Los Altos, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/045,427

(22) Filed: Mar. 10, 2011

(65) Prior Publication Data

US 2011/0201002 A1    Aug. 18, 2011

Related U.S. Application Data

(60) Division of application No. 12/174,488, filed on Jul. 16, 2008, now Pat. No. 7,919,249, which is a continuation of application No. 10/879,493, filed on Jun. 28, 2004, now Pat. No. 7,572,581.

(60) Provisional application No. 60/483,861, filed on Jun. 30, 2003.

(51) Int. Cl.
    C12Q 1/68          (2006.01)
(52) U.S. Cl. ........................................ 435/6.1
(58) Field of Classification Search .................. None
    See application file for complete search history.

(56) References Cited

U.S. PATENT DOCUMENTS

| 4,458,066 | A |   | 7/1984  | Caruthers et al. |       |
|-----------|---|---|---------|------------------|-------|
| 4,469,863 | A |   | 9/1984  | Ts'o et al.      |       |
| 5,034,506 | A |   | 7/1991  | Summerton et al. |       |
| 5,216,141 | A |   | 6/1993  | Benner           |       |
| 5,235,033 | A |   | 8/1993  | Summerton et al. |       |
| 5,386,023 | A |   | 1/1995  | Sanghvi et al.   |       |
| 5,532,130 | A |   | 7/1996  | Alul             |       |
| 5,547,835 | A | * | 8/1996  | Koster ............ | 435/6 |
| 5,602,240 | A |   | 2/1997  | De Mesmaeker et al. |    |
| 5,637,684 | A |   | 6/1997  | Cook et al.      |       |
| 5,644,048 | A |   | 7/1997  | Yau              |       |
| 5,939,292 | A | * | 8/1999  | Gelfand et al. ......... | 435/91.2 |
| 5,945,312 | A | * | 8/1999  | Goodman et al. ........ | 435/91.1 |
| 5,990,303 | A |   | 11/1999 | Seela            |       |
| 6,495,671 | B1|   | 12/2002 | Manoharan et al. |       |
| 2001/0041794 | A1 |   | 11/2001 | Bischofberger et al. |   |
| 2007/0154914 | A1 |   | 7/2007  | Gelfand et al.   |       |

FOREIGN PATENT DOCUMENTS

| EP | 2007008997 | | 10/2007 |
|----|-----------|---|---------|
| WO | 9416101 | A2 | 7/1994 |
| WO | 9416101 | A3 | 7/1994 |
| WO | 9830992 | A2 | 7/1998 |
| WO | 9830992 | A3 | 7/1998 |
| WO | 9913103 | A1 | 3/1999 |
| WO | WO 9913103 | A1 * | 3/1999 |
| WO | WO 00/63366 | A2 | 10/2000 |
| WO | WO 01/90121 | A2 | 11/2001 |
| WO | WO 02/057425 | A2 | 7/2002 |
| WO | 03048387 | A2 | 6/2003 |
| WO | 03048387 | A3 | 6/2003 |
| WO | 03050298 | A1 | 6/2003 |
| WO | 2005005667 | A2 | 1/2005 |
| WO | 2005005667 | A3 | 1/2005 |
| WO | 2005118608 | A2 | 12/2005 |
| WO | 2005118608 | A3 | 12/2005 |
| WO | 2007075967 | A2 | 7/2007 |
| WO | 2007075967 | A3 | 7/2007 |

OTHER PUBLICATIONS

Ono et al. (Nucleic Acids Res. Nov. 15, 1997;25(22):4581-8).*
Tang et al. (Anal. Chem., 1997, 69 (3), 302-312).*
Ono et al. (Nucleic Acids Res. Nov. 15, 1997;25(22):4581-4588).*
Carroll et al. (J Biol Chem. Apr. 4, 2003;278(14):11979-84. Epub Jan. 27, 2003).*
Hamel ("Derivatives of guanosine triphosphate with ribose 2'-hydroxyl substituents. Interactions with the protein synthetic enzymes of *Escherichia coli*" Eur J Biochem. Nov. 15, 1976;70(2):339-47).*
Cashel, Michael, 1974, "Preparation of Guanosine Tetraphosphate (ppGpp) and Guanosine Pentaphosphate (pppGpp) from *Escherichia coli* Ribosomes", Analytical Biochemistry, 57:100-107.
Hamel, Ernest, 1976, "Derivatives of Guanosine Triphosphate with Ribose 2'Hydroxyl Substituents: Interactions with the Protein Synthetic Enzymes of *Escherichia coli*", Eur. J. Biochem, 70:229-347.
Zhang, Jia, et al., 2005 "Proofreading genotyping assays mediated by high fidelity exo + DNA polymerases", Trends in Biotechnology, 23(2):92-96.
Cashel, Michael, et al., 1976, "Interactions of ppGpp Structural Analogs with RNA Polymerase", Alfred Benzon Symposium, 9:279-291.
Hamel ("Derivatives of guanosine triphosphate with ribose 2'-hydroxyl substituents. Interactions with the protein synthetic enzymes of *Escherichia coli*" Eur J Biochem. Nov. 15, 1976;70(2):339-47).
U.S. Appl. No. 60/519,661, filed Nov. 12, 2003, Gelfand et al.
Adams et al. (1969) "Nucleotide sequence from the coat protein cistron of R17 bacteriophage RNA." *Nature* 223(210): 1009-1014.
Beaucage and Iyer (1993) "The Functionalization of Oligonucleotides via Phosphoramidite Derivative." *Tetrahedron* 49(10): 1926-1963.
Beaucage and Caruthers (1981) "Deoxynucleoside Phosphoramidites—A New Class of Key Intermediates for Deoxypolynucleotide Synthesis." *Tetrahedron Letters*. 22:1859-1862.
Brill et al. (1989) "Synthesis of Oligodeoxynucleoside Phosphorodithioates via Thioamid." *Journal of American Chemistry Society* 111:2321-2323.
Brown et al. (1979) "Chemical synthesis and Cloning of a Tyrosine tRNA Gene." *Methods in Enzymology* 68:109-151.
Brownlee et al. (1967) "Molecular Structure: Nucleotide Sequence of 5S-ribosomal RNA from *Escherichia coli.*" *Nature* 215(102): 735-736.

(Continued)

Primary Examiner — Christopher M. Babic
(74) Attorney, Agent, or Firm — David J. Chang

(57) ABSTRACT

The present invention provides methods of extending primer nucleic acids and sequencing target nucleic acids. The methods include the use of 2'-terminator nucleotides to effect chain termination. In addition to related reaction mixtures and kits, the invention also provides computers and computer readable media.

24 Claims, 8 Drawing Sheets

OTHER PUBLICATIONS

Carlsson et al. (1996) 'Screening for Genetic Mutations. *Nature* 380:207.

Carroll et al. (2003) "Inhibition of Hepatitis C Virus RNA Replication by 2'-Modified Nucleoside Analogs." *The Journal of Biological Chemistry* 278(14): 11979-11984.

Denpcy et al. (1995) "Synthesis of a Thymidyl Pentamer of Deoxyribonucleic Guanidine and Binding Studies with DNA Homopolynucleotides." *Proceedings of the National Academy of Scliences USA* 92: 6097-6101.

Egholm et al. (1992) "Peptide nucleic acids (PNA). Oligonucleotide analogs with an achiral peptide backbone." *al of American Chemistry Society* 114:1895-1897.

Egholm et al. (1993) "PNA hybridizes to complementary oligonucleotides obeying the Watson-Crick hydrogen-bonding rules." *Nature* 365:566-568.

Gao and Jeffs (1994) "Unusual conformation of a 3'-thioformacetal linkage in a DNA duplex." *Journal of Biomolecular NMR* 4:17-34.

Gilbert and Maxam (1973) The nucleotide sequence of the lac operator *Proceedings of the National Academy of Sciences USA* 70(12): 3581-3584.

Grein et al. (1994) "3-Deaza- and 7-Deazapurines: Duplex Stability of Oligonucleotides Containing Modified Adenine or Guanine Bases." *Bioorganic Medicinal Chemistry Letters* 4(8): 971-976.

Horn et al. (1996) "Oligonucleotides with alternating anionic and cationic phosphoramidate linkages: Synthesis and hybridization of stereo-uniform isomers." *Tetrahedron Letters* 37:743-764.

Jenkins and Turner (1995) "The Biosynthesis of Carbocyclic." *Chemical Society Review* 169-176.

Jung et al. (1994) "Hybridization of Alternating Cationic.Anionic Oligonucleotieds to RNA Segments." *Nucleoside & Nucleotide* 13(6 &7):1597-1605.

Kiedrowski et al. (1991) "Parabolic Growth of a Self-Replicating Hexadeoxynucleotide Bearing a 3'-5'-Phosphamidate Linkage." *Angew. Chem. Int. Ed. English* 30: 423-426.

Lee et al. (1992) "DNA sequencing with dye-labeled terminators and T7 DNA polymerase: effect of dyes and dNTPs on incorporation of dye-terminators and probability analysis of termination fragments," *Nucleic Acid Res.* 20:2471-2483.

Letsinger (1970) "Phosphoramidate Analogs of Oligonucleotides." *Journal of Organic Chemistry* 35(11): 3800-3803.

Letsinger et al. (1986) "Effects of pendant groups at phosphorus on binding properties of d-ApA analogues." *Nucleic Acids Research* 14: 3487-3499.

Letsinger et al. (1988) "Cationic oligonucleotides." *Journal of American Chemistry Society* 10:4470-4471.

Mag et al. (1991) "Synthesis and selective cleavage of an oligodeoxynucleotide containing a bridged internucleotide 5'-phosphorothioate linkage." *Nucleic Acids Research* 19(7):1437-1441.

Matteucci et al. (1981) "Total solid-phase synthesis of porcine gut gastrin releasing peptide (GRP), a mammalian bombesin." *Journal of American Chemistry Society* 103:3185-3191.

Maxam and Gilbert (1977) A new method for sequencing DNA *Proceedings of the National Academy of Sciences USA* 74:560-564.

Meier and Engles (1992) "Peptide Nucleic Acids (PNAs)—Unusual Properties of Nonionic Oligonucleotide Analogues." *Angew. Chem. Int. Ed. English* 31(8):1008-1010.

Mesmaeker et al. (1994) "Comparison of Rigid and Flexible Backbones in Antisense Oligonucleotides." *Bioorganlc & Medicinal Chemistry Letters* 4(3): 395-398.

Narang et al. (1979) "Improved Phosphotriester Method for the Synthesis of Gene Fragments." *Methods in Enzymology* 68:90-99.

Pauwels et al. (1986) "Biological Activity of New 2-5A Analogues." *Chemica Scripta* 26: 141-145.

Sanger et al. (1973) "Use of DNA polymerase I primed by a synthetic oligonucleotide to determine a nucleotide sequence in phage fl DNA," *Proceedings of the National Academy of Sciences USA* 70(4): 1209-1213.

Sanger et al. (1977) "DNA sequencing with chain-terminating inhibitors," *Proceedings of the National Academy of Sciences USA* (74)12: 5463-5467.

Sanger et al. (1992) "DNA sequencing with chain-terminating inhibitors," *Milestones in Biotechnology* pp. 104-108.

Sanghvi and Cook (1994) ASC Symposium Series 580, "Carbohydrate Modifications in Antisense Research", Ed. Chapters 2 and 3.

Sauer et al. (2002) "Facile method for automated genotyping of single nucleotide polymorphisms by mass spectrometry," *Nucleic Acids Research* 30(5):e22.

Sawai (1984) "Synthesis and Properties of Oligoadenylic Acids Containing 2'-5' Phosphoramide Linkage." *Chemistry Letters*, pp. 805-808.

Seela and Becher (1999) "Oligonucleotides Containing Pyrazolo[3,4-α] pyrimidines: The Influence of 7-Substituted 8-Aza-7-deaza-2'-deoxyguanosines on the Duplex Structure and Stability." *Helvetica Chimic Acta* 82:1640-1655.

Seela and Lampe (1991) "3-Deazaguanine $N^7$—and $N^9$—(2'-Deoxy-β-D-ribofuranosides): Building Blocks for Solid-Phase Synthesis and Incorporation into Oligodeoxyribonucleotides." *Helvetica Chimic Acta* 74:1790-1800.

Smith et al. (1986) "Fluorescence detection in automated DNA sequence analysis," *Nature* 321:674-679.

Sprinzl et al. (1977) "Enzymatic Incorporation of ATP and CTP Analogues into the 3' End of tRNA." *European Journal of Biochemistry* 81:579-589.

Moore et al. (2002) "Synthesis of Nucleotide Analogues That Potently and Selectively Inhibit Humna DNA Primase." *Biochemistry* 41:14066-14075.

WO US2004/21075 International Preliminary Examination Report, Roche Diagnostics GmbH, Jul. 3, 2007.

Messens, E., et al. (1968) "The Synthesis of Nucleoside 2' (3')-Phosphate 5'-Triphosphates," *FEBS Letters*, vol. 1, No. 5: 326-328.

\* cited by examiner

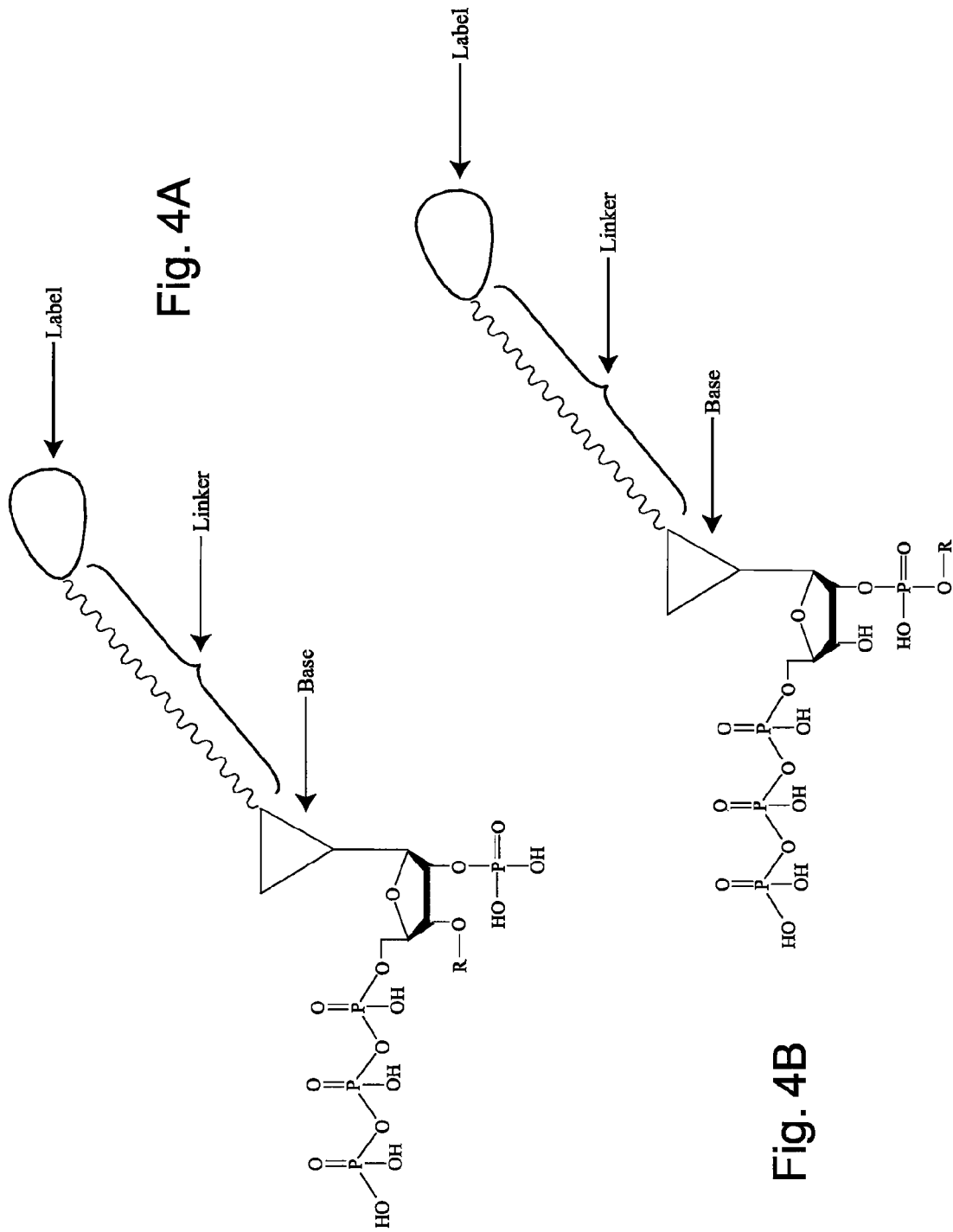

SEQUENCE LISTING

<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: synthetic oligonucleotide
<220> FEATURE:
<221> NAME/KEY: misc_feature
<222> LOCATION: (19)..(19)
<223> OTHER INFORMATION: n is 2'-amino (ribo) C

<400> SEQUENCE: 1
cgccagggtt ttcccagtna                                        20

2'-TERMINATOR NUCLEOTIDE-RELATED METHODS AND SYSTEMS

CROSS-REFERENCES TO RELATED APPLICATIONS

This application is a divisional of U.S. application Ser. No. 12/174,488 filed on Jul. 16, 2008, now U.S. Pat. No. 7,919,249, which is a continuation of U.S. application Ser. No. 10/879,493, filed on Jun. 28, 2004, now, U.S. Pat. No. 7,572,581, which claims the benefit of U.S. Provisional Application No. 60/483,861, filed Jun. 30, 2003, the disclosures of which are all incorporated by reference by their entirety for all purposes.

COPYRIGHT NOTIFICATION

Pursuant to 37 C.F.R. §1.71(e), Applicants note that a portion of this disclosure contains material, which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention relates generally to nucleic acid chemistry and molecular biology. More specifically, the invention provides nucleic acid sequencing and labeling methods in addition to other related aspects that involve 2'-terminator nucleotides.

BACKGROUND OF THE INVENTION

Nucleic acid sequencing involves the determination of the sequence of nucleotides of a particular nucleic acid molecule. Knowledge of the sequence of a nucleic acid molecule is typically fundamental to elucidating the function of the molecule and facilitating manipulation of the molecule. Further, variations in individual genomes often account for differences in susceptibility to diseases and pharmacological responses to treatment. To illustrate, changes in a single base of a nucleic acid molecule, which are commonly referred to as single nucleotide polymorphisms (SNPs), can affect an individual's risk for a given disease. By comparing these variations, for example, researchers are gaining an understanding of the medical utility of SNPs, thereby enhancing our ability to effectively diagnose, prognosticate, and treat disease.

Nucleic acid sequencing technology began in the late 1960s with efforts to sequence RNA. In particular, the sequence of 5S-ribosomal RNA from *Escherichia coli* (Brownlee et al. (1967) "Nucleotide sequence of 5S-ribosomal RNA from *Escherichia coli*," *Nature* 215(102):735) and R17 bacteriophage RNA coding for coat protein (Adams et al. (1969) "Nucleotide sequence from the coat protein cistron of R17 bacteriophage RNA," *Nature* 223(210):1009) are some of the early examples of RNA sequencing. Subsequently, Sanger described the sequencing of bacteriophage f1 DNA by primed synthesis with DNA polymerase (Sanger et al. (1973) "Use of DNA polymerase I primed by a synthetic oligonucleotide to determine a nucleotide sequence in phage f1 DNA," *Proc. Natl. Acad. Sci. USA* 70(4):1209), while Gilbert and Maxam reported on the DNA nucleotide sequence of the lac operator (Gilbert and Maxam (1973) "The nucleotide sequence of the lac operator," *Proc. Natl. Acad. Sci. USA* 70(12):3581).

In 1977, Sanger described the use of modified nucleoside triphosphates (including dideoxyribose) in combination with deoxyribonucleotides to terminate chain elongation (Sanger et al. (1977) "DNA sequencing with chain-terminating inhibitors,"*Biotechnology* 24:104). In that same year, Maxam and Gilbert reported a method for sequencing DNA that utilized chemical cleavage of DNA preferentially at guanines, at adenines, at cytosines and thymines equally, and at cytosines alone (Maxam and Gilbert (1977) "A new method for sequencing DNA,"*Proc. Natl. Acad. Sci. USA* 74:560). These two methods accelerated manual sequencing based on electrophoretic separation of DNA fragments labeled with radioactive markers and subsequent detection via autoradiography.

The Sanger dideoxy method for sequencing DNA has become far more widely used than the Maxam-Gilbert chemical cleavage method. The Sanger method includes the synthesis of a new strand of DNA starting from a specific priming site and ending with the incorporation of a chain terminating or terminator nucleotide. In particular, a DNA polymerase extends a primer nucleic acid annealed to a specific location on a DNA template by incorporating deoxynucleotides (dNTPs) complementary to the template. Synthesis of the new DNA strand continues until the reaction is randomly terminated by the inclusion of a dideoxynucleotide (ddNTP). These nucleotide analogs are incapable of supporting further chain extension since the ribose moiety of the ddNTP lacks the 3'-hydroxyl necessary for forming a phosphodiester bond with the next incoming dNTP. This produces a population of truncated sequencing fragments, each with a defined or fixed 5'-end and a varying 3'-end. Among the disadvantages of the dideoxy method is the expense associated with making ddNTPs.

Two frequently used automated sequencing methodologies are dye-primer nucleic acid and dye-terminator sequencing. These methods are suitable for use with fluorescent label moieties. Although sequencing can also be done using radioactive label moieties, fluorescence-based sequencing is increasingly preferred. Briefly, in dye-primer sequencing, a fluorescently labeled primer is used in combination with unlabeled ddNTPs. The procedure typically utilizes four synthesis reactions and up to four lanes on a gel for each template to be sequenced (one corresponding to each of the base-specific termination products). Following primer nucleic acid extension, the sequencing reaction mixtures containing dideoxynucleotide-incorporated termination products are routinely electrophoresed on a DNA sequencing gel, Following separation by electrophoresis, the fluorescently-labeled products are excited in the gel with a laser and the fluorescence is detected with an appropriate detector. In automated systems, a detector scans the bottom of the gel during electrophoresis, to detect whatever label moiety has been employed, as the reactions pass through the gel matrix (Smith et al. (1986) "Fluorescence detection in automated DNA sequence analysis," *Nature* 321:674). In a modification of this method, four primers are each labeled with a different fluorescent marker. After the four separate sequencing reactions are completed, the mixtures are combined and the reaction is subjected to gel analysis in a single lane, and the different fluorescent tags (one corresponding to each of the four different base-specific termination products) are individually detected.

Alternatively, dye-terminator sequencing methods are employed. In this method, a DNA polymerase is used to incorporate dNTPs and fluorescently labeled ddNTPs onto the growing end of a DNA primer (Lee et al. (1992) "DNA sequencing with dye-labeled terminators and T7 DNA polymerase: effect of dyes and dNTPs on incorporation of dye-terminators and probability analysis of termination fragments," *Nucleic Acid Res.* 20:2471). This process offers the advantage of not having to synthesize dye-labeled primers. Furthermore, dye-terminator reactions are more convenient in that all four reactions can be performed in the same tube.

Other methods of deconvoluting sequencing reaction mixtures include the use of gas phase ion spectrometry. For example, matrix assisted laser desorption/ionization time-of-flight mass spectrometry (MALDI-TOF-MS) is one approach that has been successfully utilized in high-throughput sequencing and SNP genotyping analyses (see, e.g., Sauer et al. (2002) "Facile method for automated genotyping of single nucleotide polymorphisms by mass spectrometry," *Nucleic Acids Res.* 30(5):e22.

From the foregoing, it is apparent that additional methods of sequencing and genotyping nucleic acids are desirable. The present invention provides new nucleic acid sequencing methods that utilize 2'-terminator nucleotides, as well as a variety of additional features including approaches to nucleic acid labeling that will be apparent upon a complete review of the following disclosure.

SUMMARY OF THE INVENTION

The present invention provides methods of sequencing and labeling nucleic acids that utilize 2'-terminator nucleic acids, e.g., instead of ddNTPs, acyclo nucleotide triphosphates, or other types of nucleic acid extension terminators. The 2'-terminator nucleotides of the invention, which have intact sugar rings (e.g., pentose sugar rings) or sugar analog rings (e.g., carbocyclic rings, etc.), include blocking groups (e.g., a negatively charged blocking group, a bulky blocking group, and/or the like) at 2'-positions of those sugar moieties. In addition, the nucleotide incorporating biocatalysts comprise the ability to extend primer or other nucleic acids with these 2'-terminator nucleotides (e.g., a 2'-phosphate-3'-hydroxyl NTP or NDP, etc.) at the 3' end of the primer nucleic acids in, e.g., a template directed manner (i.e., incorporate the 2'-terminator nucleotides into the primer nucleic acids). Certain nucleotide incorporating biocatalysts referred to herein, such as terminal deoxynucleotidyl transferase (TdT; EC 2.7.7.31), polynucleotide phosphorylase (PNPase; EC 2.7.7.8), etc. are generally able to extend nucleic acids in a template independent manner. Upon incorporation of a 2'-terminator nucleotide at the 3'-terminal end of a primer nucleic acid, the nucleic acid is typically rendered non-extendible by a nucleotide incorporating biocatalyst of the invention. Furthermore, an extended primer nucleic acid comprising a 2'-terminator nucleotide is also generally resistant to proofreading enzymatic activity (e.g., a 3'-5' exonuclease activity, etc.). Thus, a nucleotide incorporating biocatalyst utilized in a method of the invention optionally includes a 3)-5' exonuclease activity, e.g., to improve sequence fidelity relative to approaches that utilize catalysts lacking or having diminished proofreading activities. In addition to methods, the invention also provides reaction mixtures, kits, systems, computers, and computer readable media relating to the 2'-nucleotides described herein. The present invention provides an economical alternative to pre-existing terminator methods. The 2'-terminator nucleotides of the invention are readily substituted in various sequencing, end labeling, or other protocols without sacrificing ease of use.

More specifically, one aspect of the present invention relates to a method of extending a primer nucleic acid. The method includes incubating a template nucleic acid (e.g., DNA, RNA, etc.) with at least one nucleotide incorporating biocatalyst, at least one 2'-terminator nucleotide (e.g., a 2'-monophosphate-3'-hydroxyl-5'-triphosphate nucleoside, etc.), and at least one primer nucleic acid that is at least partially complementary to at least a subsequence of the template nucleic acid. The primer nucleic acid generally comprises DNA. The nucleotide incorporating biocatalyst extends the primer nucleic acid to produce at least one extended primer nucleic acid, incorporating the 2'-terminator nucleotide at a terminal end of the extended primer nucleic acid. In some embodiments, the template nucleic acid is incubated with the nucleotide incorporating biocatalyst, the 2'-terminator nucleotide, and the primer nucleic acid in solution, whereas in others, either the primer nucleic acid or the template nucleic acid is covalently or non-covalently attached to a solid support.

In certain embodiments of the invention, the method further includes detecting a molecular mass of the extended primer nucleic acid or a fragment thereof. In these embodiments, a genotype of the template nucleic acid is determinable from the detected molecular mass of the extended primer nucleic acid or the fragment thereof. The molecular mass is typically detected using gas phase ion spectrometry (e.g., MALDI-TOF-mass spectrometry or another version of gas phase ion spectrometry).

The 2'-terminator nucleotide, the extended primer nucleic, and/or the primer nucleic acid optionally comprises at least one label (e.g., a fluorescent dye, a radioisotope, a mass-modifying group, etc.). In these embodiments, the method generally further includes detecting a detectable signal produced by the label (e.g., spectrophotometrically, etc) such that a genotype of the template nucleic acid is determinable from the detected signal. For example, the label is optionally attached, e.g., to a heterocyclic base of the 2'-terminator nucleotide, a sugar moiety of the 2'-terminator nucleotide, and/or a phosphate group of the 2'-terminator nucleotide. Optionally, a linker attaches the label to the 2'-terminator nucleotide.

The method of extending a primer nucleic acid optionally also includes incubating the template nucleic acid with at least one extendible nucleotide (e.g., a ribonucleotide, a deoxyribonucleotide, and/or the like). In these embodiments, the nucleotide incorporating biocatalyst typically produces multiple different extended primer nucleic acids and the method also generally includes resolving the multiple different extended primer nucleic acids such that at least a portion of a base sequence of the template nucleic acid is determinable from the resolved extended primer nucleic acids. For example, the extended primer nucleic acids are optionally resolved by determining the molecular masses, sizes, and/or charge properties of the extended primer nucleic acids. In certain embodiments, the extended primer nucleic acids further comprise labels and the extended primer nucleic acids are resolved by separating the labeled extended primer nucleic acids from each other and detecting detectable signals produced by the labels. To illustrate, the labeled extended primer nucleic acids are separated by at least one separation technique, such as electrophoresis, chromatography, and gas phase ion spectrometry (e.g., MALDI-TOF-mass spectrometry or another version of gas phase ion spectrometry).

In other aspects, the invention provides a method of extending a nucleic acid, e.g., to end label the nucleic acid and/or for other applications. The method includes incubating at least one nucleic acid with at least one nucleotide incorporating biocatalyst (e.g., a terminal transferase, a polynucleotide phosphorylase, etc.) and at least one labeled 2'-terminator nucleotide. The nucleotide incorporating biocatalyst extends the nucleic acid to produce at least one extended nucleic acid by incorporating the labeled 2'-terminator nucleotide at a terminal end (e.g., a 3' terminal end) of the nucleic acid. In certain embodiments, the method further includes hybridizing the extended nucleic acid with another nucleic acid and detecting a detectable signal produced by the label.

In some embodiments, the nucleic acid comprises a primer nucleic acid that is at least partially complementary to at least a subsequence of a template nucleic acid, and the method comprises incubating the template nucleic acid with the nucleotide incorporating biocatalyst, the labeled 2'-terminator nucleotide, and the primer nucleic acid. In these embodiments, the nucleotide incorporating biocatalyst typically comprises an enzyme selected from, e.g., a polymerase, a terminal transferase, a reverse transcriptase, a polynucleotide phosphorylase, a telomerase, and the like. To illustrate, the nucleotide incorporating biocatalyst optionally comprises a modified enzyme (e.g., a G46E E678G CS5 DNA polymerase, a G46E E678G CS6 DNA polymerase, an E615G Taq DNA polymerase, a Δ ZO5R polymerase, a G46E L329A E678G CS5 DNA polymerase, etc). Typically, the method further includes incubating the template nucleic acid with at least one extendible nucleotide. In these embodiments, the nucleotide incorporating biocatalyst generally produces multiple different extended primer nucleic acids and the method comprises resolving the multiple different extended primer nucleic acids. At least a portion of a base sequence of the template nucleic acid is typically determinable from the resolved extended primer nucleic acids. Typically, the extended primer nucleic acids are resolved by determining the molecular masses, sizes, and/or charge properties of the extended primer nucleic acids. For example, the extended primer nucleic acids are optionally resolved by separating the extended primer nucleic acids from each other and detecting detectable signals produced by the labels.

In another aspect, the invention relates to a method of inhibiting further extension of an extended nucleic acid, e.g., to treat a host infected with a pathogenic agent or the like. The method includes contacting at least one nucleic acid (e.g., microbial DNA, viral RNA, etc.) with at least one nucleotide incorporating biocatalyst and at least one 2'-terminator nucleoside or nucleotide, or a pharmaceutically acceptable salt thereof. The nucleic acid generally comprises DNA or RNA. In addition, the 2'-terminator nucleoside or nucleotide, or pharmaceutically acceptable salt thereof, is non-extendible by the nucleotide incorporating biocatalyst. The nucleotide incorporating biocatalyst extends the nucleic acid to produce at least one extended nucleic acid by incorporating the labeled 2'-terminator nucleoside or nucleotide, or the pharmaceutically acceptable salt thereof, at a terminal end of the nucleic acid, thereby inhibiting further extension of the extended nucleic acid. To illustrate, when the nucleic acid comprises microbial DNA, the nucleotide incorporating biocatalyst, and the 2'-terminator nucleoside or nucleotide, or the pharmaceutically acceptable salt thereof, are generally contacted in a host infected with a microbe that comprises the microbial DNA.

In another aspect, the invention provides a method of sequencing a target nucleic acid. The method includes (a) incubating the target nucleic acid with one or more polymerases, one or more 2'-monophosphate-3'-hydroxyl nucleosides (e.g., 2'-monophosphate-3'-hydroxyl-5'-triphosphate nucleosides, 2'-monophosphate-3'-hydroxyl-5'-diphosphate nucleosides, etc.), one or more extendible nucleotides, and one or more primers that are complementary to at least a subsequence of the target nucleic acid. The polymerases extend the primers to produce primer extension products that incorporate the 2'-monophosphate-3'-hydroxyl nucleosides at 3'-terminal ends of the primer extension products. In some embodiments, (a) comprises incubating the target nucleic acid, the polymerases, the extendible nucleotides, and the primer nucleic acids with at least two different 2'-monophosphate-3'-hydroxyl nucleosides. In other embodiments, (a) comprises multiple separate reactions in which at least two of the reactions comprise different 2'-monophosphate-3'-hydroxyl nucleosides. In these embodiments, the different 2'-monophosphate-3'-hydroxyl nucleosides optionally comprise different labels. The method also includes (b) identifying the 2'-monophosphate-3'-hydroxyl nucleosides in the primer extension products such that at least a portion of a base sequence of the target nucleic acid is determinable from the identified 2'-monophosphate-3'-hydroxyl nucleosides. For example, (b) optionally comprises determining the molecular masses of the primer extension products or 3'-terminal fragments thereof and the sequence of the target nucleic acid from the molecular masses. The molecular masses are generally determined using gas phase ion spectrometry. In some embodiments, the primer extension products comprise labels and (b) comprises separating the primer extension products from each other and detecting detectable signals produced by the labels. The primer extension products are typically separated by one or more separation techniques including, e.g., electrophoresis, chromatography, gas phase ion spectrometry, etc.

In still other aspects, the invention provides a reaction mixture comprising at least one labeled 2'-terminator nucleotide as described herein (e.g., a 2'-monophosphate-3'-hydroxyl nucleoside, such as a 2'-monophosphate-3'-hydroxyl-5'-triphosphate nucleoside, a 2'-monophosphate-3'-hydroxyl-5'-diphosphate nucleoside, etc.) and at least one nucleotide incorporating biocatalyst as described herein. In some embodiments, the reaction mixture also includes at least one pyrophosphatase (e.g., a thermostable pyrophosphatase, etc.). The reaction mixture optionally further includes one or more extendible nucleotides (e.g., ribonucleotides, deoxyribonucleotides, and/or the like). Optionally, at least one of the extendible nucleotides is labeled. In certain embodiments, the reaction mixture also includes a template nucleic acid and a primer nucleic acid that is at least partially complementary to at least a subsequence of the template nucleic acid. Optionally, the template nucleic acid or the primer nucleic acid is attached (e.g., covalently or noncovalently) to a solid support. In some of these embodiments, the primer comprises a label. For example, a label utilized as described herein optionally comprises a fluorescent dye (e.g., selected from fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, and BODIPY®-family dyes).

In another aspect, the invention provides a kit for extending a nucleic acid (e.g., to label the nucleic acid, to sequence target nucleic acids, etc.). The kit includes (a) at least one nucleotide incorporating biocatalyst as described herein, and (b) at least one labeled 2'-terminator nucleotide as described herein. For example, the 2'-terminator nucleotide comprises at least one label (e.g., enzymes (e.g., alkaline phosphatase and horseradish peroxidase) and enzyme substrates, radioactive moieties, fluorescent moieties, chromophores, chemiluminescent labels, electrochemiluminescent labels, such as Origin™ (Igen), mass-modifying groups, ligands having specific binding partners, etc.). In some embodiments, the kit further includes one or more extendible nucleotides and optionally, at least one of the extendible nucleotides comprises a label. Optionally, the kit further includes at least one pyrophosphatase, such as a thermostable pyrophosphatase.

Typically, the kit also includes (c) a set of instructions for extending the primer nucleic acid with the nucleotide incorporating biocatalyst and the 2'-terminator nucleotide. Further, the kit optionally also includes (d) at least one container for packaging the nucleotide incorporating biocatalyst, the 2'-terminator nucleotide, and the set of instructions. In certain embodiments, the kit further includes a template nucleic acid and the primer nucleic acid, which primer nucleic acid is complementary to at least a subsequence of the template nucleic acid. Optionally, the template nucleic acid or the primer nucleic acid is attached to a solid support. In some of these embodiments, the primer comprises a label, such as a radioisotope, a fluorescent dye, a mass-modifying group, or the like.

In other aspects, the invention relates to a system for extending a primer nucleic acid. The system includes (a) at least one container comprising a labeled 2'-terminator nucleotide. Typically, the system comprises a plurality of containers. The system also includes (b) at least one thermal modulator operably connected to the container to modulate temperature in the container, and/or (c) at least one fluid transfer component that transfers fluid to and/or from the container. The system optionally further includes at least one detector operably connected to the container to detect detectable signals produced in the container. The system typically further includes at least one controller operably connected to the thermal modulator to effect modulation of the temperature in the container and/or to the fluid transfer component to effect transfer of the fluid to and/or from the container.

In other aspects, the invention provides computer or computer readable medium comprising a data set that comprises at least one character corresponding to at least one labeled 2'-terminator nucleotide as described herein. Typically, the data set comprises a plurality of character strings corresponding to a plurality of nucleic acid sequences.

BRIEF DESCRIPTION OF THE DRAWINGS

FIGS. 4 A and B schematically show labeled nucleotide tetraphosphates according to certain embodiments of the invention.

DETAILED DISCUSSION OF THE INVENTION

I. DEFINITIONS

Figure 1B:
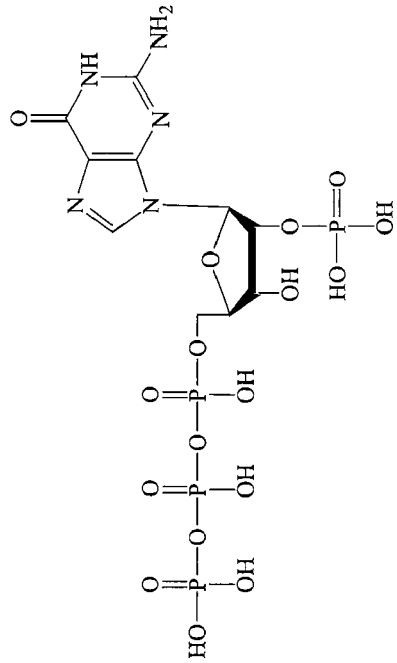
FIGS. 1A-D schematically illustrate 2'-terminator nucleotides according to certain embodiments of the invention.

Before describing the present invention in detail, it is to be understood that this invention is not limited to particular methods, reaction mixtures, systems, computers, or computer readable media, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set out below.

The term "nucleic acid" refers to nucleotides (e.g., ribonucleotides, deoxyribonucleotides, 2'-terminator nucleotides, dideoxynucleotides, etc.) and polymers (e.g., comprising deoxyribonucleoic acids (DNAs), ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), PNA-DNA conjugates, PNA-RNA conjugates, etc.) that comprise such nucleotides covalently linked together, either in a linear or branched fashion.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925) and references therein; Letsinger (1970) *J. Org. Chem.* 35:3800; Sprinzl et al. (1977) *Eur. T. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321), O-methylphosphoroamidite linkages (see Eckstein, *Oligonucleotides and Analogues: A Practical Approach*, Oxford University Press (1992)), and peptide nucleic acid backbones and linkages (see, Egholm (1992) *J. Am. Chem. Soc.* 114:1895; Meier et al, (1992) *Chem. Int. Ed. Engl.* 31:1008; Nielsen (1993) *Nature* 365:566; Carlsson et al. (1996) *Nature* 380:207), which references are each incorporated by reference. Other analog nucleic acids include those with positively charged backbones (Denpcy et al. (1995) *Proc. Natl. Acad. Sci. USA* 92: 6097); non-ionic backbones (U.S. Pat. Nos. 5,386,023, 5,637, 684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994)*J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) *Chem. Soc. Rev.* pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

An "oligonucleotide" refers to a nucleic acid that includes at least two nucleotides, typically more than three nucleotides, and more typically greater than ten nucleotides. The exact size of an oligonucleotide generally depends on various factors, including the ultimate function or use of the oligonucleotide. Oligonucleotides are optionally prepared by any suitable method, including, for example, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al, (1981) *J. Am. Chem. Soc.* 103: 3185-3191; automated synthesis methods; or the solid support method of U.S. Pat. No. 4,458,066, among other methods known in the art, which references are each incorporated by reference.

A "primer nucleic acid" is typically a nucleic acid that can hybridize to a template nucleic acid and permit chain extension or elongation using, e.g., a nucleotide incorporating biocatalyst, such as a thermostable polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. A primer nucleic acid can be labeled, if desired, by incorporating a label detectable by, e.g., spectroscopic, photochemical, biochemical, immunochemical, or chemical techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art, In addition, a primer nucleic acid can simply provide a substrate for a nucleotide incorporating biocatalyst in a template independent manner.

An "extended primer nucleic acid" refers to a primer nucleic acid to which one or more additional nucleotides have been added or otherwise incorporated (e.g., covalently bonded to).

A "template nucleic acid" refers to a nucleic acid to which a primer nucleic acid can hybridize and be extended. Accordingly, template nucleic acids include subsequences that are at least partially complementary to the primer nucleic acids. Template nucleic acids can be derived from essentially any source. To illustrate, template nucleic acids are optionally derived or isolated from, e.g., cultured microorganisms, uncultured microorganisms, complex biological mixtures, tissues, sera, pooled sera or tissues, multispecies consortia, ancient, fossilized or other nonliving biological remains, environmental isolates, soils, groundwaters, waste facilities, deep-sea environments, or the like. Further, template nucleic acids optionally include or are derived from, e.g., individual cDNA molecules, cloned sets of cDNAs, cDNA libraries, extracted RNAs, natural RNAs, in vitro transcribed RNAs, characterized or uncharacterized genomic DNAs, cloned genomic DNAs, genomic DNA libraries, enzymatically fragmented DNAs or RNAs, chemically fragmented DNAs or RNAs, physically fragmented DNAs or RNAs, or the like. Template nucleic acids can also be chemically synthesized using techniques known in the art. In addition, template nucleic acids optionally correspond to at least a portion of a gene or are complementary thereto. As used herein, a "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extendible nucleotide" refers to a nucleotide to which at least one other nucleotide can be added or covalently bonded, e.g., in a reaction catalyzed by a nucleotide incorporating biocatalyst once the extendible nucleotide is incorporated into a nucleotide polymer. Examples of extendible nucleotides include deoxyribonucleotides and ribonucleotides. An extendible nucleotide is typically extended by adding another nucleotide at a 3'-position of the sugar moiety of the extendible nucleotide.

A "non-extendible" nucleotide refers to a nucleotide, which upon incorporation into a nucleic acid prevents further extension of the nucleic acid, e.g., by at least one nucleotide incorporating biocatalyst.

A "2'-terminator nucleotide" refers to a nucleotide analog that comprises a blocking group (BG) at the 2'-position of the sugar moiety of the nucleotide. A "blocking group" refers to a chemical group or moiety that typically prevents the extension of a nucleic acid (i.e., a 2'-terminator nucleotide is typically non-extendible by one or more nucleotide incorporating biocatalysts). That is, once a 2'-terminator nucleotide is incorporated into a nucleic acid (e.g., at a 3'-terminal end of the nucleic acid), the blocking group prevents further extension of a nucleic acid by at least one nucleotide incorporating biocatalyst selected from, e.g., a G46E E678G CS5 DNA polymerase, a G46E L329A E678G CS5 DNA polymerase, G46E E678G CS6 DNA polymerase, Δ ZO5R DNA polymerase, ZO5 polymerase, E615G Taq DNA polymerase, *Thermus flavus* (Tfl) polymerase (e.g., a modified Tfl polymerase that incorporates the 2'-terminator nucleotides described herein), *Thermatoga maritime-* or Tma-25 polymerase, Tma-30 polymerase, *Thermus thermophilus* (Tth) DNA polymerase, *Thermus* specie SPS-17 polymerase, E615G Taq polymerase, *Thermus* ZO5R polymerase, T7 DNA polymerase, Kornberg DNA polymerase I or *E. coli* DNA Polymerase I, Klenow DNA polymerase, Taq DNA polymerase, Micrococcal DNA polymerase, alpha DNA polymerase, reverse transcriptase, AMV reverse transcriptase, M-MuLV reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase (PNP), ribonucleotide incorporating DNA polymerase, and/or the like. An exemplary blocking group is a phosphate group. Other representative blocking groups are also described herein. Exemplary 2'-terminator nucleotides include 2'-monophosphate-3'-hydroxyl-5'-triphosphate nucleosides and 2'-monophosphate-3'-hydroxyl-5'-diphosphate nucleosides. Other 2'-terminator nucleotides are also described further herein and in, e.g., U.S. Provisional Application No. 60/519,661, entitled "SYNTHESIS AND COMPOSITIONS OF 2'-TERMINATOR NUCLEOTIDES," filed Nov. 12, 2003 by Gelfand et al., which is incorporated by reference.

A "tetraphosphate nucleotide" refers to a nucleotide that includes four phosphate groups. Exemplary tetraphosphate nucleotides include 2'-monophosphate-5'-triphosphate nucleosides and 3'-monophosphate-5'-triphosphate nucleosides.

A "negatively charged blocking group" refers to a blocking group that comprises at least one negative charge, which negative charge at least contributes to the non-extendible property of the nucleotide to which it is attached, e.g., by electrostatic repulsion of incoming nucleotides. To illustrate, negatively charged blocking groups at the 2'-positions of nucleotides of the invention optionally include phosphate, carboxy, or other groups referred to herein that typically comprise at least one negative charge upon ionization. In certain embodiments, multiple factors can contribute to the non-extendible property of a nucleotide of the invention including, e.g., blocking group charge and size.

A "bulky blocking group" refers to a blocking group comprising sufficient size to sterically hinder the incorporation of an incoming nucleotide, thereby at least contributing to the non-extendible property of the nucleotide to which the blocking group is attached. As noted above, in some embodiments of the invention, multiple factors can contribute to the non-extendible property of a 2'-terminator nucleotide including, e.g., blocking group charge and size.

A "moiety" or "group" refers to one of the portions into which something, such as a molecule, is divided (e.g., a functional group, substituent group, or the like). For example, a nucleotide typically comprises a basic group (e.g., adenine, thymine, cytosine, guanine, uracil, or an analog basic group), a sugar moiety (e.g., a moiety comprising a sugar ring or an analog thereof), and one or more phosphate groups.

A "mass modifying" group modifies the mass, typically measured in terms of molecular weight as daltons, of a molecule that comprises the group. For example, mass modifying groups that increase the discrimination between at least two nucleic acids with single base differences in size or sequence can be used to facilitate sequencing using, e.g., molecular weight determinations.

A "heterocyclic ring" refers to a monocyclic or bicyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "homocyclic ring" refers to a saturated or unsaturated (but not aromatic) carbocyclic ring, such as cyclopropane, cyclobutane, cyclopentane, cyclohexane; cycloheptane, cyclohexene, and the like.

An "alkyl group" refers to a linear, branched, or cyclic saturated hydrocarbon moiety and includes all positional isomers, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkenyl group" refers to a linear, branched, or cyclic unsaturated hydrocarbon moiety that comprises one or more carbon-carbon double bonds. Exemplary alkenyl groups include ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-2-propenyl, and the like. An alkenyl group typically comprises about 1-20 carbon atoms and more typically comprises about 2-15 carbon atoms. Alkenyl groups can be substituted or unsubstituted.

An "alkynyl group" refers to a linear, branched, or cyclic unsaturated hydrocarbon moiety that comprises one or more carbon-carbon triple bonds. Representative alkynyl groups include, e.g., 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl 1-ethyl-1-methyl-2-propynyl, and the like. An alkynyl group typically comprises about 1-20 carbon atoms and more typically comprises about 2-15 carbon atoms. Alkynyl groups can be substituted or unsubstituted.

An "alkoxy group" refers to an alkyl group that comprises an oxygen atom and includes, e.g., methoxy, ethoxy, propoxy, butoxy, pentoxy, heptyloxy, octyloxy, and the like.

A "halo group" refers to a group that comprises a halogen atom, such as F, Cl, Br, or I.

An "aryl group" refers to a substituent group of atoms or moiety that is derived from an aromatic compound. Exemplary aryl groups include, e.g., phenyl groups, benzyl groups, tolyl groups, xylyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

An "alkyl-aryl group" refers to a group that comprises alkyl and aryl moieties.

An "ether group" refers to a linear, branched, or cyclic moiety that comprises two carbon atoms attached to a single oxygen atom. Exemplary ether groups include, e.g., methoxymethyl, methoxyethyl, methoxypropyl, ethoxyethyl, and the like.

A "thioether group" refers to a linear, branched, or cyclic moiety that comprises two carbon atoms attached to a single sulfur atom and includes, e.g., methylthiomethyl, methylthioethyl, methylthiopropyl, and the like.

An "alkylamine group" refers to an amino group that comprises at least one alkyl group.

An "alkenylamine group" refers to an amino group that comprises at least one alkenyl group.

An "alkynylamine group" refers to an amino group that comprises at least one alkynyl group.

An "ester group" refers to a class of organic compounds that includes the general formula RCOOR', where R and R' are independently selected from an alkyl group, an alkenyl group, an alkynyl group, an aryl group, or combinations thereof.

A "polyaminoacid" refers to compound or group that comprises two or more amino acid residues. Exemplary polyaminoacids include peptides, polypeptides, proteins, and the like.

A "heterooligo" refers to an oligonucleotide that comprises two or more different nucleotide residues.

A "heterooligo/polyaminoacid group" refers to a hybrid group that comprises both at least one heterooligo moiety and at least one polyaminoacid moiety.

An "aldehyde group" refers to an organic group that includes the formula CHO.

An "alcohol group" refers to an organic group that includes at least one hydroxy group.

A "silyl group" refers to a class of compounds that includes the general formula SiRR'R", where R, R', and R" are independently an H, an alkyl group, an alkenyl group, an alkynyl group, an aryl group, or a combination of such groups.

A "sequence" of a nucleic acid refers to the order and identity of nucleotides in the nucleic acid. A sequence is typically read in the 5' to 3' direction.

A "full-length sequence" refers to a nucleic acid sequence that comprises at least substantially the same number of nucleotides as a reference sequence or a nucleic acid sequence that is at least partially complementary to the reference sequence. In certain embodiments of the invention, for example, an extended primer nucleic acid is complementary to a full-length sequence of a template nucleic acid or other reference sequence.

A "subsequence" or "fragment" refers to any portion of an entire nucleic acid sequence.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

The term "attached" refers to interactions including, but not limited to, covalent bonding, ionic bonding, chemisorption, physisorption, and combinations thereof.

A "linker" or "spacer" refers to a chemical moiety that covalently or non-covalently (e.g., ionically, etc.) attaches a compound or substituent group to, e.g., a solid support, another compound or group, or the like. For example, a linker optionally attaches a label (e.g., a fluorescent dye, a radioisotope, etc.) to a 2'-terminator nucleotide or the like. Linkers are typically bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support, another compound, etc. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Additional description of linker molecules is provided in, e.g., Lyttle et al. (1996) *Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, Pljevaljcic et al. (2003) *J. Am. Chem. Soc.* 125(12): 3486, Ward, et. al., U.S. Pat. No. 4,711,955, Stavrianopoulos, U.S. Pat. No. 4,707,352, and Stavrianopoulos, U.S. Pat. No. 4,707,440, which are each incorporated by reference.

A "nucleotide incorporating biocatalyst" refers to a catalyst that catalyzes the incorporation of nucleotides into a nucleic acid. Nucleotide incorporating biocatalysts are typically enzymes. An "enzyme" is a protein-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like. Other biocatalysts may be DNA-based ("DNAzymes") or RNA-based ("ribozymes").

A "thermostable enzyme" refers to an enzyme that is stable to heat (i.e., resists breakdown or denaturation) and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683, 195, which are both incorporated by reference. As used herein, a thermostable polymerase is typically suitable for use in a temperature cycling reaction such as the polymerase chain reaction ("PCR"). For a thermostable nucleotide incorporating enzyme, enzymatic activity refers to the catalysis of the combination of the nucleotides in the proper manner to form primer extension products that are complementary to a template nucleic acid. Other thermostable enzymes referred to herein, include thermostable pyrophosphatases, which similarly retain sufficient activity when subjected to elevated temperatures, e.g., to minimize pyrophosphorolysis. Similarly to enzymes, DNAzymes and ribozymes may also be thermostable.

A "modified" enzyme refers to an enzyme comprising a monomer sequence in which at least one monomer of the sequence differs from a monomer in a reference sequence, such as a native or wild-type form of the enzyme or another modified form of the enzyme, e.g., when the two sequences are aligned for maximum identity. Exemplary modifications include monomer insertions, deletions, and substitutions. The modified enzymes (i.e., protein- or nucleic acid-based catalysts) of the invention have been or are optionally created by various diversity generating methods. Although essentially any method can be used to produce a modified enzyme, certain exemplary techniques include recombining (e.g., via recursive recombination, synthetic recombination, or the like) two or more nucleic acids encoding one or more parental enzymes, or by mutating one or more nucleic acids that encode enzymes, e.g., using recursive ensemble mutagenesis, cassette mutagenesis, random mutagenesis, in vivo mutagenesis, site directed mutagenesis, or the like. A nucleic acid encoding a parental enzyme typically includes a gene that, through the mechanisms of transcription and translation, produces an amino acid sequence corresponding to a parental enzyme, e.g., a native form of the enzyme. Modified enzymes also include chimeric enzymes that have identifiable component sequences (e.g., structural and/or functional domains, etc.) derived from two or more parents. Also included within the definition of modified enzymes are those comprising chemical modifications (e.g., attached substituent groups, altered substituent groups, etc.) relative to a reference sequence. Similarly to enzymes, DNAzymes and ribozymes may also comprise similar modifications.

A "label" refers to a moiety attached (covalently or non-covalently), or capable of being attached, to a molecule, which moiety provides or is capable of providing information about the molecule (e.g., descriptive, identifying, etc. information about the molecule). Exemplary labels include fluorescent labels, weakly fluorescent labels, non-fluorescent labels, colorimetric labels, chemiluminescent labels, bioluminescent labels, radioactive labels, mass-modifying groups, antibodies, antigens, biotin, haptens, and enzymes (including, e.g., peroxidase, phosphatase, etc.).

A "solid support" refers to a solid material which can be derivatized with, or otherwise attached to, a chemical moiety, such as a primer nucleic acid, a template nucleic acid, or the like. Exemplary solid supports include a plate, a bead, a microbead, a fiber, a whisker, a comb, a hybridization chip, a membrane, a single crystal, a ceramic layer, a self-assembling monolayer, and the like.

The phrase "in solution" refers to a reaction condition in which at least the reactants are not attached to a solid support. For example, certain extension reactions of the invention include incubating template nucleic acids, primer nucleic acids, 2'-terminator nucleotides, extendible nucleotides, and nucleotide incorporating biocatalysts together in solution.

The term "cleavage" refers to a process of releasing a material or compound from another compound or material or from a solid support, e.g., to permit analysis of the compound by solution-phase methods. See, e.g., Wells et al. (1998) "Cleavage and Analysis of Material from Single Resin Beads," *J. Org. Chem.* 63:6430-6431.

A "character" when used in reference to a character of a character string refers to a subunit of the string. In a preferred embodiment, the character of a character string encodes one subunit of an encoded biological molecule. Thus, for example, where the encoded biological molecule is a polynucleotide or oligonucleotide, a character of the string encodes a single nucleotide.

A "character string" represents any entity capable of storing sequence information (e.g., the subunit structure of a biological molecule such as the nucleotide sequence of a nucleic acid, etc.). In one embodiment, the character string can be a simple sequence of characters (letters, numbers, or other symbols) or it can be numeric representation of such information in tangible or intangible (e.g., electronic, magnetic, etc.) form. The character string need not be "linear," but can also exist in a number of other forms, e.g., a linked list or other non-linear array (e.g., used as a code to generate a linear array of characters), or the like. Character strings are preferably those which encode polynucleotide strings, directly or indirectly, including any encrypted strings, or images, or arrangements of objects which can be transformed unambiguously to character strings representing sequences of monomers or multimers in polynucleotides, or the like (whether made of natural or artificial monomers).

The term "resolve" refers to the identification of one or more properties of at least certain members of a given population. In some embodiments of the invention, for example, nucleotide incorporating biocatalysts produce multiple different extended primer nucleic acids, which are resolved such that at least a portion of a base sequence of a template nucleic acid is determinable from the resolved extended primer nucleic acids. To further illustrate, a population of extended primer nucleic acids is optionally resolved by determining the molecular masses, sizes, and/or charge properties of the individual extended primer nucleic acids in the population. In some embodiments, labeled extended primer nucleic acids are resolved by separating the extended primer nucleic acids in a population and detecting detectable signals produced by the labels.

The phrase "gas phase ion spectrometry" refers to the use of a gas phase ion spectrometer to detect gas phase ions. Gas phase ion spectrometers typically include an ion source that supplies gas phase ions, Gas phase ion spectrometers include, mass spectrometers, total ion current measuring devices, ion mobility spectrometers, and the like.

A "mass spectrometer" is an analytical instrument that can be used to determine the molecular weights of various substances, such as products of an enzyme catalyzed reaction. Typically, a mass spectrometer comprises four parts: a sample inlet, an ionization source, a mass analyzer, and a detector. A sample is optionally introduced via various types of inlets, e.g., solid probe, gas chromatography (GC), or liquid chromatography (LC), in gas, liquid, or solid phase. The sample is then typically ionized in the ionization source to form one or more ions. The resulting ions are introduced into and manipulated by the mass analyzer (e.g., a time-of-flight (TOF) mass analyzer, etc.). Surviving ions are detected based on mass to charge ratios. In one embodiment, the mass spectrometer bombards the substance under investigation with a laser or electron beam and quantitatively records the result as a spectrum of positive and negative ion fragments. Separation of the ion fragments is on the basis of mass to charge ratio of the ions. If all the ions are singly charged, this separation is essentially based on mass. A quadrupole mass spectrometer uses four electric poles for the mass analyzer. These techniques are described further in many texts including, e.g., Dawson, *Quadrupole Mass Spectrometry and its Applications*, Springer Verlag, (1995). In an electrospray mass spectrometry system, ionization is produced by an electric field that is used to generate charged droplets and subsequent analyte ions by ion evaporation. See, Cole "Electrospray Ionization Mass Spectrometry" John Wiley and Sons, Inc. (1997).

A "mixture" refers to a combination of two or more different components. A "reaction mixture" refers a mixture that comprises molecules that can participate in and/or facilitate a given reaction. For example, a "DNA sequencing reaction mixture" refers to a reaction Mixture that comprises components necessary for a DNA sequencing reaction. Thus, a DNA sequencing reaction mixture is suitable for use in a DNA sequencing method for determining the nucleic acid sequence of a template or target nucleic acid, although the reaction mixture may initially be incomplete, so that the initiation of the sequencing reaction is controlled by the user. In this manner, the reaction may be initiated once a final component, such as the enzyme, is added, to provide a complete DNA sequencing reaction mixture. Typically, a DNA sequencing reaction will contain a buffer, suitable for polymerization activity, extendible nucleotides, and at least one 2'-terminator nucleotide. The reaction mixture also may contain a primer nucleic acid suitable for extension on a template nucleic acid by a polymerase enzyme. Either the primer nucleic acid or one of the nucleotides is generally labeled with a detectable moiety such as a fluorescent label. Generally, the reaction is a mixture that comprises four extendible nucleotides and at least one 2'-terminator nucleotide. Typically, the polymerase is a thermostable DNA polymerase (e.g., a G46E E678G CS5 DNA polymerase, a G46E E678G CS6 DNA polymerase, an E615G Taq DNA polymerase, a Δ Z05RDNA polymerase, a G46E L329A E678G CS5 DNA polymerase, etc.) and the 2'-terminator nucleotide is a 2'-monophosphate-3'-hydroxyl-5'-triphosphate nucleoside.

II. 2'-TERMINATOR NUCLEOTIDES

The present invention relates generally to methods for end labeling and/or blocking template-dependent extension of nucleic acids utilizing 2'-terminator nucleotides, which typically include a hydroxyl group at a 3'-position of an intact sugar rings (e.g., pentose sugar rings) or sugar analog rings (e.g., carbocyclic rings, etc.), and a blocking group (e.g., a negatively charged blocking group, a bulky blocking group, and/or the like) at a 2'-position of the sugar moiety. The nucleotide incorporating biocatalysts of the invention comprise the ability to extend, e.g., primer nucleic acids with 2'-terminator nucleotides in a template directed manner. In certain embodiments, nucleotide incorporating biocatalysts extend nucleic acids independent of a template nucleic acid, such as when nucleic acids are end-labeled using the 2'-terminator nucleotides described herein. Upon incorporation of a 2'-terminator nucleotide at a terminal end of, e.g., an extended primer nucleic acid, the nucleic acid is typically rendered non-extendible by a nucleotide incorporating biocatalyst of the invention. Furthermore, surprisingly an extended primer nucleic acid comprising a 2'-terminator nucleotide is generally resistant to proofreading enzymatic activity (e.g., a 3'-5' exonuclease activity of a proofreading DNA polymerase, etc.). As a consequence, a nucleotide incorporating biocatalyst utilized in a method of the invention optionally includes a 3'-5' exonuclease activity, e.g., to improve sequence fidelity relative to approaches that utilize catalysts that lack or have a diminished proofreading activity. In certain embodiments of the invention, the sequencing methods utilize a DNA polymerase that lacks an F to Y mutation in helix O of the enzyme or otherwise lacks a mutation that enhances incorporation of 3'-deoxynucleotides by the enzyme.

Figure 1D:
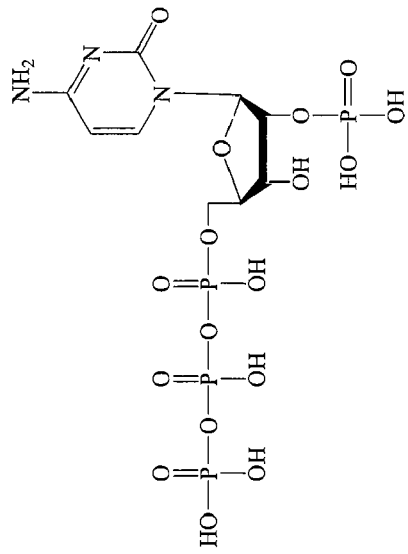
Figure 1A:
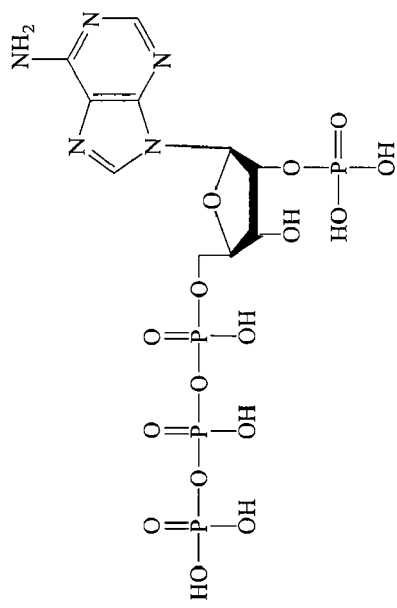
Figure 1C:
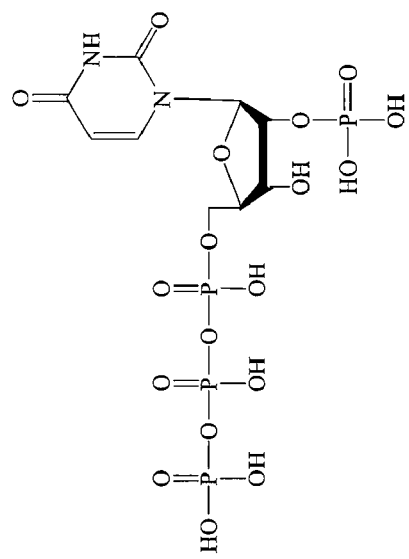

To illustrate, FIGS. 1A-D schematically depict 2'-terminator nucleotides according to certain embodiments of the invention. In particular, FIG. 1A schematically shows an adenosine tetraphosphate terminator nucleoside, FIG. 1B schematically depicts a guanosine tetraphosphate terminator nucleoside, FIG. 1C schematically illustrates a uridine tetraphosphate terminator nucleoside, and FIG. 1D schematically shows a cytidine tetraphosphate terminator nucleoside.

A 2'-terminator nucleotide according to the present invention generally includes the formula:

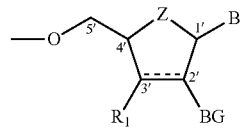

in which $R_1$ is H, OH, a hydrophilic group, or a hydrophobic group; B is at least one homocyclic ring, at least one heterocyclic ring (with or without exocyclic heteroatoms), or at least one aryl group, or combinations thereof; BG is a blocking group; Z is O or $CH_2$; and ----represents a single or double bond. In certain embodiments, a nucleotide of the invention is labeled. Further, a 2'-terminator nucleotide generally comprises 1, 2, 3, or more phosphate groups attached at the 5' position. In one embodiment of the invention, for example, the nucleotide comprises a 2'-monophosphate-3'-hydroxyl-5'-triphosphate nucleoside.

The 2'-terminator nucleotides of the invention optionally include essentially any heterocyclic ring or aryl group (i.e., as the base or B group). Accordingly, no attempt is made herein to describe all of the possible groups that can be utilized. However, to illustrate, B groups that base pair with another nucleic acid, e.g., via a hydrogen bond or through a base stacking mechanism are included at the 1' position of the sugar moiety of the nucleosides and nucleotides in certain embodiments of the invention. To further illustrate aspects of the invention, certain representative B groups are provided below. In some embodiments, for example, B comprises the formula:

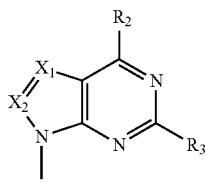

where $X_1$ and $X_2$ are independently selected from CH and N; $R_2$ is H, OH, or $NR_4R_5$; $R_3$ is H, OH, or $NR_6R_7$; $R_4$ and $R_5$ are independently selected from H, an alkyl group, an alkenyl group, an alkynyl group, a benzyl group, an aryl group, and an aryloxy group, and combinations thereof; and, $R_6$ and $R_7$ are independently selected from H, an alkyl group, an alkenyl group, an alkynyl group, a benzyl group, an aryl group, and an aryloxy group, and combinations thereof. In other embodiments, B comprises the formula:

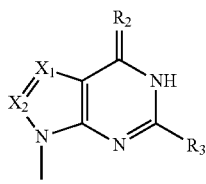

where $X_1$ and $X_2$ are independently selected from CH and N; $R_2$ is O or S; $R_3$ is H, OH, or $NR_4R_5$; and $R_4$ and $R_5$ are independently selected from H, an alkyl group, an alkenyl group, an alkynyl group, a benzyl group, an aryl group, and an aryloxy group, and combinations thereof.

In some embodiments, B comprises the formula:

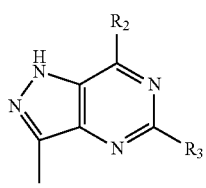

where $R_2$ is H, OH, or $NR_4R_5$; $R_3$ is H, OH, or $NR_6R_7$; $R_4$ and $R_5$ are independently selected from H, an alkyl group, an alkenyl group, an alkynyl group, a benzyl group, an aryl group, and an aryloxy group, and combinations thereof; and, $R_6$ and $R_7$ are independently selected from H, an alkyl group, an alkenyl group, an alkynyl group, a benzyl group, an aryl group, and an aryloxy group, and combinations thereof. In some embodiments, B comprises the formula:

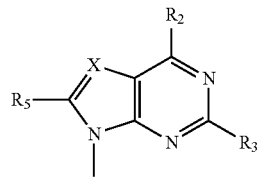

where X is CH or N; $R_2$ and $R_3$ are independently selected from H, OH, and $NHR_4$; $R_4$ is H, an alkyl group, an alkenyl group, an alkynyl group, a benzyl group, an aryl group, or an aryloxy group, or combinations thereof; and, $R_5$ is OH, $NH_2$, SH, a halo group, an ether group, a thioether group, an alkyl group, an alkenyl group, an alkynyl group, an alkylamine group, an alkenylamine group, or an alkynylamine group, or combinations thereof.

In other embodiments, B comprises the formula:

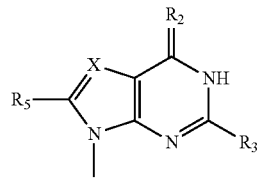

where X is CH or N; $R_2$ is O or S; $R_3$ is H, OH, or $NHR_4$; $R_4$ is H, an alkyl group, an alkenyl group, an alkynyl group, a benzyl group, an aryl group, or an aryloxy group, or combinations thereof; and $R_5$ is OH, $NH_2$, SH, a halo group, an ether group, a thioether group, an alkyl group, an alkenyl group, an alkynyl group, an alkylamine group, an alkenylamine group, or an alkynylamine group, or combinations thereof. In certain embodiments, B comprises the formula:

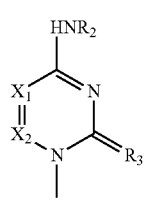

where $X_1$ and $X_2$ are independently selected from CH and N; $R_2$ is H, an alkyl group, an alkenyl group, an alkynyl group, a benzyl group, an aryl group, or an aryloxy group, or combinations thereof; and $R_3$ is O or S. In other embodiments, B comprises the formula:

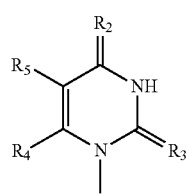

where $R_2$ and $R_3$ are independently selected from O and S; and $R_4$ and $R_5$ are independently selected from H, $NH_2$, SH, OH, an alkyl group, an alkenyl group, an alkynyl group, a benzyl group, an aryl group, an aryloxy group, an alkoxy group, and a halo group, and combinations thereof. In some embodiments, B comprises the formula:

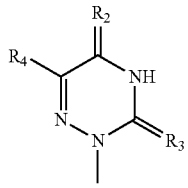

where $R_2$ and $R_3$ are independently selected from O and S; and $R_4$ is H, $NH_2$, SH, OH, an alkyl group, an alkenyl group, an alkynyl group, a benzyl group, an aryl group, an aryloxy group, an alkoxy group, or a halo group, or combinations thereof. In other embodiments, B comprises the formula:

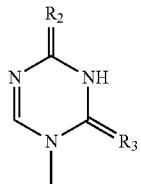

where $R_2$ and $R_3$ are independently selected from O and S. In some embodiments, B comprises the formula:

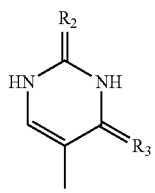

where $R_2$ and $R_3$ are independently selected from O and S. In other embodiments, B comprises the formula:

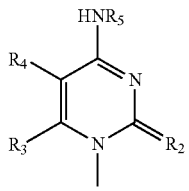

where $R_2$ is O or S; $R_3$ and $R_4$ are independently selected from H, $NH_2$, SH, OH, COOH, $COOCH_3$, $COOCH_2CH_3$, CHO, $NO_2$, CN, an alkyl group, an alkenyl group, an alkynyl group, a benzyl group, an aryl group, an aryloxy group, an alkoxy group, a halo group, and combinations thereof; and $R_5$ is an alkyl group, an alkoxy group, an alkenyl group, an alkenoxy group, an alkynyl group, an alkynoxy group, an aryl group, an aryloxy group, a benzyl group, a benzyloxy group, or combinations thereof.

Figure 2B:
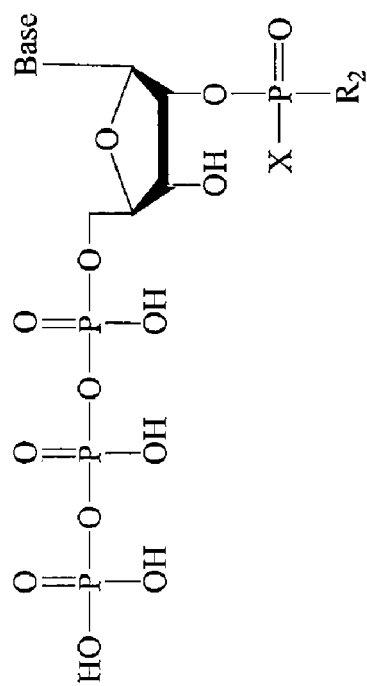
FIGS. 2 A and B schematically show 2'-terminator nucleotides according to some embodiments of the invention.
Figure 2A:
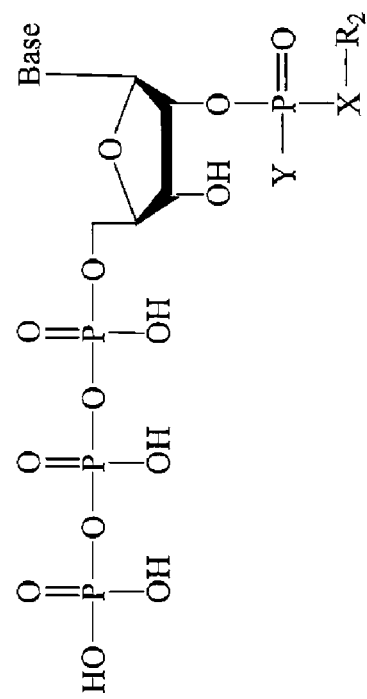

The blocking groups (BG) utilized at the 2' position of the sugar moiety also include various embodiments. In some embodiments, for example, BG is a negatively charged group and/or a bulky group. To further illustrate, BG is optionally selected from, e.g., CN, $NO_2$, $N_3$, a silyl group, a halo group, an alcohol group, an ether group, an aldehyde group, an acidic group, an ester group, an amino group, and combinations thereof. More specifically, BG optionally comprises the formula:

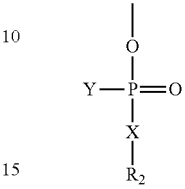

where X is O, S, $NR_3$, $CR_3R_4$, or $SiR_3R_4$; Y is $CR_5R_6R_7$, $SiR_5R_6R_7$, $OR_5$, $SR_5$, or $NHR_5$; $R_2$ is H, OH, $NHR_8$, $SR_8$, an alkyl group, a benzyl group, an aryl group, an alkenyl group, an alkynyl group, an alkoxy group, or combinations thereof; and $R_3$, $R_4$, $R_5$, $R_6$, $R_7$, and $R_8$ are independently selected from H, an alkyl group, a benzyl group, an aryl group, an alkenyl group, an alkynyl group, or combinations thereof. FIG. 2A schematically depicts one nucleotide comprising a blocking group having this formula. To further illustrate, BG optionally comprises the formula:

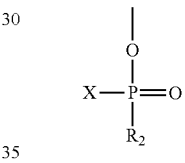

where X is $CR_3R_4R_5$, $SiR_3R_4R_5$, $OR_3$, $SR_3$, or $NHR_3$; $R_2$ is H, $NHR_6$, $SR_6$, an alkyl group, a benzyl group, an aryl group, an alkenyl group, an alkynyl group, an alkoxy group, or combinations thereof; and $R_3$, $R_4$, $R_5$, and $R_6$ are independently selected from H, an alkyl group, a benzyl group, an aryl group, an alkenyl group, an alkynyl group, or combinations thereof. FIG. 2B schematically depicts one 2'-terminator nucleotide comprising a blocking group having this formula.

The 2'-terminator nucleotides, extendible nucleotides, primer nucleic acids (e.g., extended primer nucleic acids), and/or other nucleic acids utilized according to the methods of the invention optionally comprise at least one label. For example, the label is optionally attached, e.g., to a homocyclic ring, a heterocyclic ring, or an aryl group of the 2'-terminator nucleotide (e.g., via $C^5$ of a pyrimidine, $N^4$ of cytidine, $N^7$ of a purine, $N^6$ of adenosine, $C^8$ of a purine, or another attachment site known in the art), e.g., through an amide, ester, thioester, ether, thioether, carbon-carbon, or other type of covalent bond. In addition, or alternatively, the label is attached to a sugar moiety (e.g., a ribose sugar, etc.), or an analog thereof (e.g., a carbocyclic ring, etc.), of a 2'-terminator nucleotide, and/or a phosphate group of a 2'-terminator nucleotide, such as by a covalent bond that is an amide, ester, thioester, ether, thioether, carbon-carbon, or other bond. Covalent bonds are typically formed in reactions between electrophilic and nucleophilic groups of labels and nucleotides of the invention. In certain embodiments, labels and nucleotides are directly conjugated to one another (e.g., via single, double, triple or aromatic carbon-carbon bonds, or via carbon-nitrogen bonds, nitrogen-nitrogen bonds, carbon-oxygen bonds, carbon-sulfur bonds, phosphorous-oxygen bonds, phosphorous-nitrogen bonds, etc.). Optionally, a linker attaches the label to the 2'-terminator nucleotide. A wide variety of linkers can be used or adapted for use in conjugating labels and nucleotides. Certain non-limiting illustrations of such linkers referred to herein.

Figure 3A:
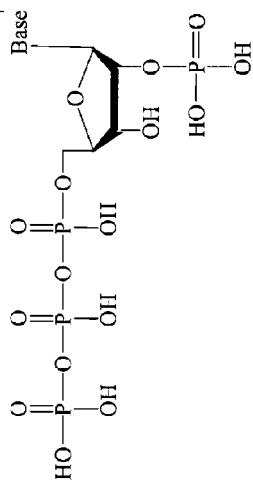
FIGS. 3A-C schematically illustrate dye labeled tetraphosphates according to various embodiments of the invention.
Figure 3B:
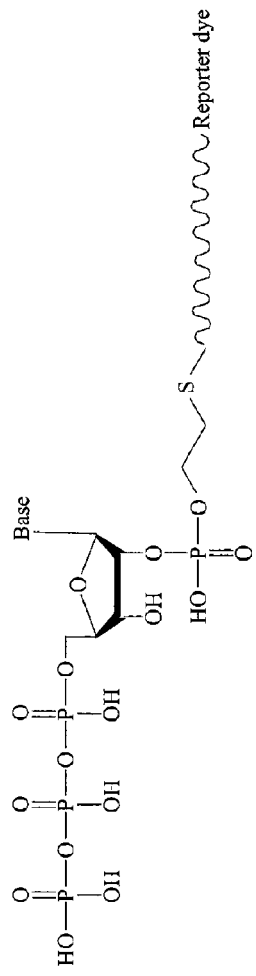
Figure 3C:
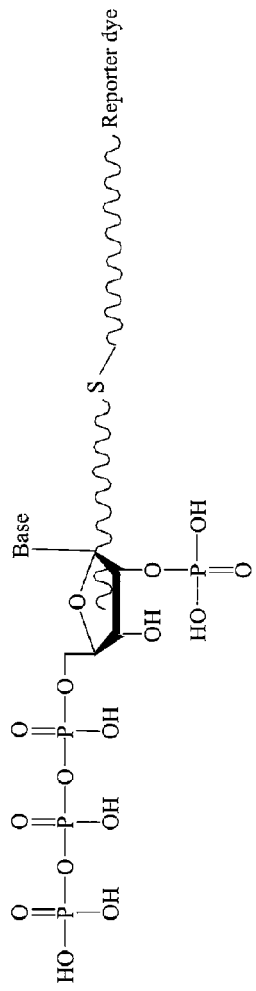
Figure 5:
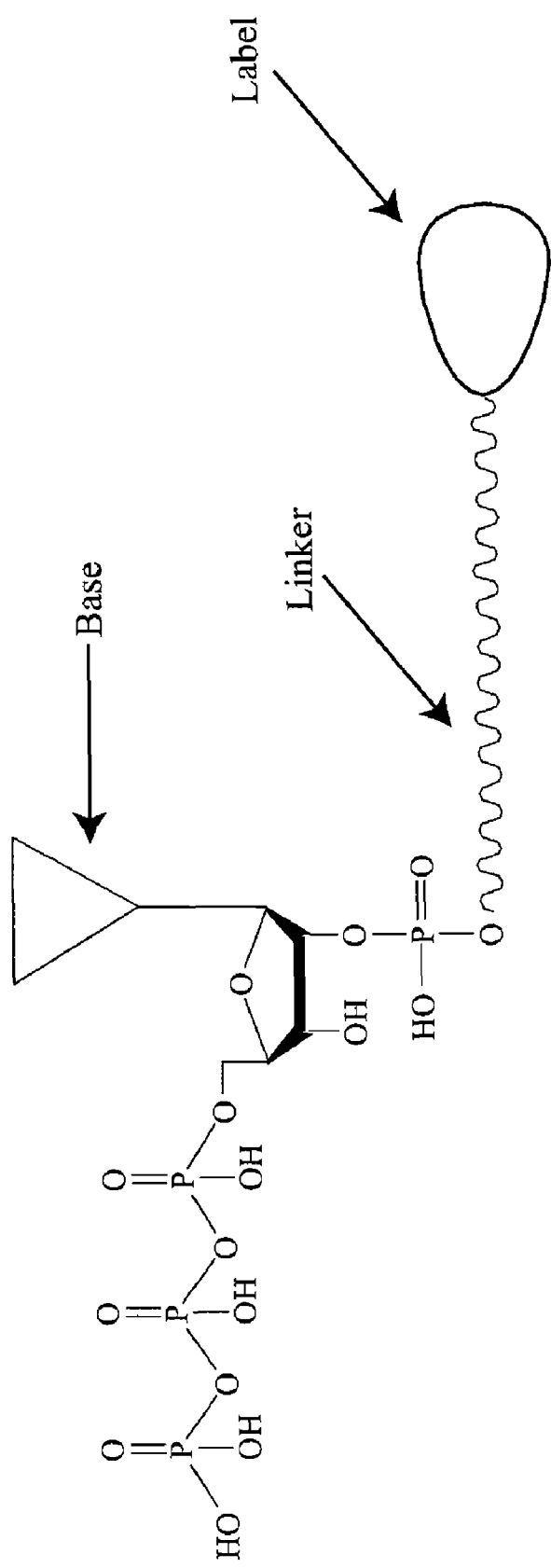
FIG. 5 schematically depicts a label attached to a nucleotide tetraphosphate via a linker according to one embodiment of the invention.
Figure 6A:
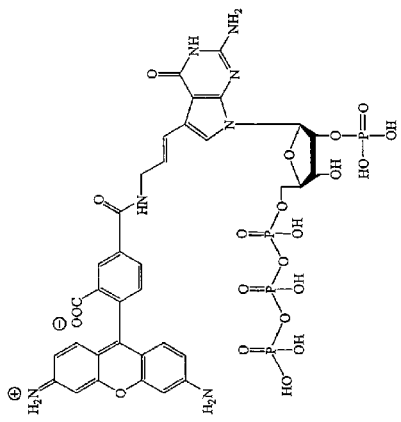
FIG. 6A-D schematically show various 2'-terminator nucleotides having attached fluorescent dyes according to certain embodiments of the invention.
Figure 6B:
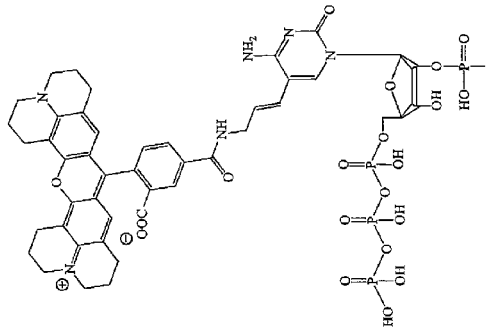
Figure 6C:
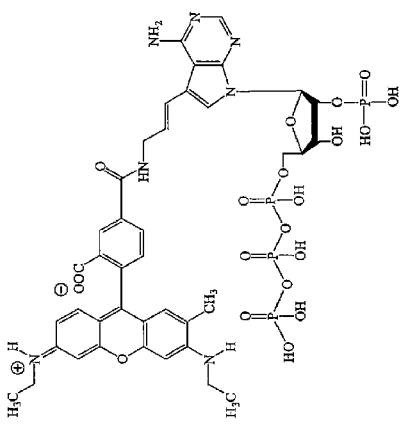
Figure 6D:
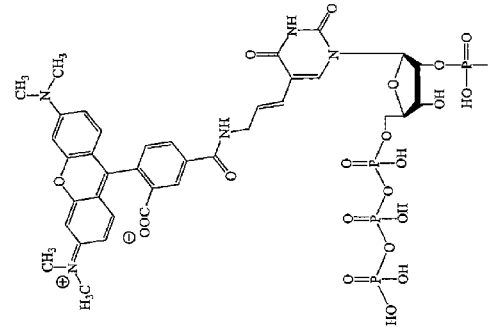

To further illustrate, FIGS. 3A-C schematically illustrate dye labeled tetraphosphates according to certain embodiments of the invention. In particular, FIG. 3A schematically shows a reporter dye attached to a base of a 2'-terminator nucleotide, FIG. 3B schematically depicts a reporter dye attached to a blocking group of a 2'-terminator nucleotide, and FIG. 3C schematically shows a reporter dye attached to a sugar moiety a 2'-terminator nucleotide. FIGS. 4A and B also schematically show labeled nucleoside tetraphosphates according to some embodiments of the invention. More specifically, FIGS. 4A and B schematically show labels attached via linkers to bases of the nucleoside tetraphosphates, where R is selected from the group consisting of: H, OH, an alkyl group, an aryl group, a branched alkyl group, a branched alkyl-aryl group, an alkenyl group, and an alkynyl group. In addition, FIG. 5 schematically depicts a label attached to a nucleoside tetraphosphate via a linker according to one embodiment of the invention. FIG. 6A-D also schematically show various 2'-terminator nucleotides having attached fluorescent dyes according to certain embodiments of the invention. In particular, FIG. 6A schematically shows an R6G-labeled adenosine tetraphosphate, FIG. 6B schematically depicts an R110-labeled guanosine tetraphosphate, FIG. 6C schematically illustrates a TAMRA-labeled uridine tetraphosphate, and FIG. 6D schematically shows an ROX-labeled cytidine tetraphosphate.

Essentially any label is optionally utilized to label the nucleotides and nucleosides of the invention. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional details relating to fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128 (5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference.

In certain embodiments, the label comprises a radioisotope, such as $^{3}H$, $^{14}C$, $^{22}Na$, $^{32}P$, $^{33}P$, $^{35}S$, $^{42}K$, $^{45}Ca$, $^{59}Fe$, $^{125}I$, $^{203}Hg$, or the like. To further exemplify, the label also optionally includes at least one mass-modifying group. For example, the mass-modifying group is optionally selected from, e.g., deuterium, F, Cl, Br, I, S, $N_3$, XY, $CH_3$, $SPO_4$, $BH_3$, $SiY_3$, $Si(CH_3)_3$, $Si(CH_3)_2(C_2H_5)$, $Si(CH_3)(C_2H_5)_2$, $Si(C_2H_5)_3$, $(CH_2)_nCH_3$, $(CH_2)_nNY_2$, $CH_2CONY_2$, $(CH_2)_n$ OH, $CH_2F$, $CHF_2$, $CF_3$, and a phosphorothioate group, where X is O, NH, NY, S, NHC(S), OCO(CH)$_n$COO, NHCO(CH$_2$)$_n$ COO, OSO$_2$O, OCO(CH$_2$)$_n$, NHC(S)NH, OCO(CH$_2$)$_n$S, OCO(CH$_2$)S, NC$_4$O$_2$H$_2$S, OPO(O-alkyl), or OP(O-alkyl); n is an integer from 1 to 20 inclusive; and, Y is H, deuterium, an alkyl group, an alkoxy group, an aryl group, a polyoxymethylene group, a monoalkylated polyoxymethylene group, a polyethylene imine group, a polyamide group, a polyester group, a alkylated silyl group, a heterooligo, a polyaminoacid, a heterooligo/polyaminoacid group, or a polyethylene glycol group. Additional details relating to nucleic acid labeling and sequence analysis are provided in, e.g., Sterky et al. (2000) "Sequence analysis of genes and genomes," *J. Biotech.* 76 (2000):1, Sensen (Ed.) *Biotechnology, Volume 5B, Genomics and Bioinformatics*, John Wiley & Sons, Inc. (2001), and Sensen (Ed.) *Essentials of Genomics and Bioinformatics*, John Wiley & Sons, Inc. (2002), which are each incorporated by reference.

A large variety of linkers are available for linking labels to nucleic acids and will be apparent to one of skill in the art. A linker is generally of a structure that is sterically and electronically suitable for incorporation into a nucleic acid. Linkers optionally include, e.g., ether, thioether, carboxamide, sulfonamide, urea, urethane, hydrazine, or other moieties. To further illustrate, linkers generally include between about one and about 25 nonhydrogen atoms selected from, e.g., C, N, O, P, Si, S, etc., and comprise essentially any combination of, e.g., ether, thioether, amine, ester, carboxamide, sulfonamide, hydrazide bonds and aromatic or heteroaromatic bonds. In some embodiments, for example, a linker comprises a combination of single carbon-carbon bonds and carboxamide or thioether bonds. Although longer linear segments of linkers are optionally utilized, the longest linear segment typically contains between about three to about 15 nonhydrogen atoms, including one or more heteroatoms.

Nonlimiting examples of linker moieties include substituted (e.g., functionalized) or unsubstituted groups, such as imidazole/biotin linkers, polymethylene groups, arylene groups, alkylarylene groups, arylenealkyl groups, arylthio groups, amido alkyl groups, alkynyl alkyl groups, alkenyl alkyl groups, alkyl groups, alkoxyl groups, thio groups, amino alkyl groups, morpholine derivatized phosphates, peptide nucleic acids (e.g., N-(2-aminoethyl)glycine, etc.), and the like.

Certain of these and other linkers are described further in, e.g., U.S. Pat. No. 6,339,392 to Haugland et al., U.S. Pat. No. 5,047,519 to Hobbs, Jr. et al., U.S. Pat. No. 4,711,958 to Iizuka et al., U.S. Pat. No. 5,175,269 to Stavrianopoulos, U.S. Pat. No. 4,711,955 to Ward et al., U.S. Pat. No. 5,241,060 to Engelhardt et al., U.S. Pat. No. 5,328,824 to Ward et al., and U.S. Pat. Publication No. 2002/0151711 by Khan et al., which are each incorporated by reference. Additional details relating to nucleic acid labeling and linkers are provided in, e.g., Hermanson, *Bioconjugate Techniques*, Elsevier Science (1996), which is incorporated by reference. In certain embodiments, suitable linkers comprise photocleavable moieties, such as 2-nitrobenzyl moieties, alpha-substituted 2-nitrobenzyl moieties (e.g., 1-(2-nitrophenyl)ethyl moieties), 3,5-dimethoxybenzyl moieties, thiohydroxamic acid, 7-nitroindoline moieties, 9-phenylxanthyl moieties, benzoin moieties, hydroxyphenacyl moieties, NHS-ASA moieties, and the like. Photocleavable linkers are described further in, e.g., U.S. Pat. Publication No. 2003/0099972 by Olejnik et al., which is incorporated by reference. In some embodiments, linkers include metals, such as platinum atoms. These are described further in, e.g., U.S. Pat. No. 5,714,327 to Houthoff et al., which is incorporated by reference. A number of linkers of varying lengths are commercially available from various suppliers including, e.g., Qiagen-Operon Technologies, Inc. (Alameda, Calif.), BD Biosciences Clontech (Palo Alto, Calif.), and Molecular BioSciences (Boulder, Colo.). 2'-terminator nucleotides are also described in, e.g., U.S. Provisional Application No. 60/519,661, entitled "SYNTHESIS AND COMPOSITIONS OF 2'-TERMINATOR NUCLEOTIDES," filed Nov. 12, 2003 by Gelfand et al., which is incorporated by reference.

III. LABELING AND SEQUENCING METHODS

In certain aspects, the invention provides methods of extending nucleic acids (e.g., oligonucleotides or the like), e.g., to end label the nucleic acids for use as probes among other applications. These methods typically include incubating nucleic acids to be extended with nucleotide incorporating biocatalysts (e.g., terminal transferases, polynucleotide phosphorylases, etc.) and labeled 2'-terminator nucleotides. In some embodiments, the nucleotide incorporating biocatalysts extend the nucleic acids to produce extended nucleic acids by incorporating labeled 2'-terminator nucleotides at 3' terminal ends of the nucleic acids, e.g., in a template independent manner. When the extended nucleic acids are used as probes, the methods typically further include hybridizing the extended nucleic acids with target nucleic acids and detecting detectable signals produced by the labels, thereby detecting the target nucleic acids.

In some embodiments, the methods of the invention include incubating a template nucleic acid with at least one nucleotide incorporating biocatalyst, at least one 2'-terminator nucleotide, and at least one primer nucleic acid that is at least partially complementary to at least a subsequence of the template nucleic acid. The nucleotide incorporating biocatalyst extends the primer nucleic acid to produce at least one extended primer nucleic acid, incorporating the 2'-terminator nucleotide at a terminal end of the extended primer nucleic acid.

The sequencing methods of the invention typically also include incubating the template nucleic acid with at least one extendible nucleotide (e.g., a ribonucleotide, a deoxyribonucleotide, and/or the like), which is optionally labeled. Nucleic acid labeling is described further above. Although other molar ratios are optionally utilized, the 2'-terminator nucleotides and the extendible nucleotides are typically present in a molar ratio of 1:1 or less. The extended primer nucleic acids produced by the methods of the invention are typically either complementary to a subsequence of the template nucleic acid or complementary to a full-length sequence of the template nucleic acid.

The methods of the invention also generally include incubating, e.g., the template nucleic acid with at least one pyrophosphatase (e.g., a thermostable pyrophosphatase). Pyrophosphatase has been shown to enhance sequencing results using both mesophilic polymerases and thermostable DNA polymerase by decreasing the amount of pyrophosphorolysis as extension products accumulate. In some embodiments, pyrophosphatase is not included in DNA sequencing or other reaction mixtures. More specifically, use of certain the enzymes described or referred to herein eliminates the need for the additional expense of adding a second enzyme into the sequencing reaction mixture.

In practicing the present invention, many conventional techniques in molecular biology and recombinant DNA are optionally used. These techniques are well known and are explained in, for example, *Current Protocols in Molecular Biology*, Volumes I, II, and III, 1997 (F. M. Ausubel ed.); Sambrook et al., 2001, *Molecular Cloning: A Laboratory Manual*, Third Edition, Cold Spring Harbor Laboratory Press, Cold Spring Harbor, N.Y.; Berger and Kimmel, *Guide to Molecular Cloning Techniques, Methods in Enzymology* volume 152 Academic Press. Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively).

Template nucleic acids that can be sequenced according to the methods described herein include sequences of deoxyribonucleic acid (DNA) or ribonucleic acid (RNA). These sequences can be obtained from biological, recombinant or other man-made sources, or purified from natural sources including cells, tissue or obtained from environmental sources. Other types of molecules that can be sequenced include polyamide nucleic acid (PNA) (Nielsen et al. (1991) *Science* 254:1497) or any sequence of bases joined by a chemical backbone that can form base pairs or hybridize with a complementary chemical structure.

The bases of DNA, RNA and PNA include purines, pyrimidines and purine and pyrimidine derivatives and modifications, which are linearly linked to a chemical backbone. Common chemical backbone structures are deoxyribose phosphate, ribose phosphate, and polyamide. The purines of both DNA and RNA are adenine (A) and guanine (G). Others that are known to exist include xanthine, hypoxanthine, 2- and 1-diaminopurine, and other more modified bases. The pyrimidines are cytosine (C), which is common to both DNA and RNA, uracil (U) found predominantly in RNA, and thymidine (T) which occurs almost exclusively in DNA. Some of the more atypical pyrimidines include methylcytosine, hydroxymethyl-cytosine, methyluracil, hydroxymethyluracil, dihydroxypentyluracil, and other base modifications. These bases interact in a complementary manner to form base-pairs including, e.g., guanine with cytosine and adenine with thymidine. This invention also relates to non-traditional base pairing such as Hoogsteen base pairing which has been identified in certain tRNA molecules and postulated to exist in a triple helix. Nucleic acids are described further above including in the definitional section.

Template nucleic acids are optionally purified, e.g., to remove substances which could be harmful (e.g. toxins), dangerous (e.g. infectious) or might interfere with the hybridization reaction or the sensitivity of that reaction (e.g. metals, salts, protein, lipids). Purification may involve techniques such as chemical extraction with salts, chloroform or phenol, sedimentation, centrifugation, chromatography or other techniques known to those of ordinary skill in the art.

If sufficient quantities of template nucleic acids are available and the nucleic acids are sufficiently pure or can be purified so that any substances which would interfere with hybridization are removed, then the template nucleic acids may be directly sequenced. That is, sequence information can be obtained without creating complementary or homologous copies of a target sequence. However, template nucleic acids may also be amplified, to increase the number of copies of the template using, for example, polymerase chain reactions (PCR) or another amplification technique. A nucleic acid amplification protocol is also optionally utilized to increase the number of copies of primer nucleic acid used in the methods of the invention. Nucleic acid amplification generally involves denaturation of template DNA by heating in the presence of a large molar excess of each of two or more oligonucleotide primers and four dNTPs (dGTP, dCTP, dATP, dTTP). The reaction mixture is cooled to a temperature that allows the oligonucleotide primer to anneal to target sequences, after which the annealed primers are extended with DNA polymerase. The cycle of denaturation, annealing, and DNA synthesis, the principal of PCR amplification, is repeated many times to generate large quantities of product, which can be easily identified.

Although PCR is a reliable method for amplification of template sequences, a number of other procedures can also be used including, e.g., ligase chain reaction, self sustained sequence replication, Qβ replicase amplification, polymerase chain reaction linked ligase chain reaction, gapped ligase chain reaction, ligase chain detection, rolling circle amplification, and strand displacement amplification. The principle of ligase chain reaction is based in part on the ligation of two adjacent synthetic oligonucleotide primers that uniquely hybridize to one strand of the target DNA or RNA. If the target is present, the two oligonucleotides can be covalently linked by ligase. A second pair of primers, almost entirely complementary to the first pair of primers is also provided. The template and the four primers are placed into a thermocycler with a thermostable ligase. As the temperature is raised and lowered, oligonucleotides are renatured immediately adjacent to each other on the template and ligated. The ligated product of one reaction serves as the template for a subsequent round of ligation. The presence of target is manifested as a DNA fragment with a length equal to the sum of the two adjacent oligonucleotides.

Examples of techniques sufficient to direct persons of skill through in vitro amplification methods, including the polymerase chain reaction (PCR), e.g., for the amplification of template nucleic acids in a sample or primer nucleic acids, primer nucleic acid design, etc. are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research*(1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077-1080; Van Brunt (1990) *Biotechnology* 8, 291-294; Wu and Wallace, (1989) *Gene* 4:560; Barringer et al. (1990) *Gene* 89, 117, and Sooknanan and Malek (1995) *Biotechnology* 13:563.

Template nucleic acids are optionally fragmented into a plurality of fragments using physical, chemical, or enzymatic approaches to create a set of fragments of uniform or relatively uniform length. For example, the sequences are enzymatically cleaved using, e.g., nucleases such as DNases or RNases (mung bean nuclease, micrococcal nuclease, DNase I, RNase A, RNase T1), type I or II restriction endonucleases, or other site-specific or non-specific endonucleases. Sizes of nucleic acid fragments are typically between about 5 to about 1,000 nucleotides in length, more typically between about 10 to about 200 nucleotides in length, and still more typically between about 12 to about 100 nucleotides in length. Sizes in the range of about 5, 10, 12, 15, 18, 20, 24, 26, 30 and 35 are useful to perform small scale analysis of short regions of a nucleic acid template, whereas fragment sizes in the range of 25, 50, 75, 125, 150, 175, 200 and 250 nucleotides and larger are typically useful for rapidly analyzing larger target sequences.

Primer nucleic acids, template nucleic acids, and/or other nucleic acids are optionally synthesized chemically, e.g., according to the solid phase phosphoramidite triester method described by Beaucage and Caruthers (1981) *Tetrahedron Letts.*, 22(20):1859-1862 or another synthesis technique known in the art, e.g., using an automated synthesizer, as described in Needham-VanDevanter et al. (1984) *Nucleic Acids Res.* 12:6159-6168. A wide variety of equipment is commercially available for automated oligonucleotide synthesis. Multi-nucleotide synthesis approaches (e.g., tri-nucleotide synthesis) are also optionally utilized.

In addition, essentially any nucleic acid (and virtually any labeled nucleic acid, whether standard or non-standard) can be custom or standard ordered from any of a variety of commercial sources, such as the Midland Certified Reagent Company (Midland, Tex.), the Great American Gene Company (Ramona, Calif.), ExpressGen Inc. (Chicago, Ill.), Operon Technologies Inc. (Alameda, Calif.), and many others.

Hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Hames and Higgins, supra. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, CaCl$_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen and angelicin.

In some embodiments of the invention, template nucleic acids are incubated with the nucleotide incorporating biocatalyst, the 2'-terminator nucleotide, and the primer nucleic acid in solution. In other embodiments, the template nucleic acid or the primer nucleic acid is attached (e.g., covalently or non-covalently) to a solid support. Examples of solid supports which can be used include a plastic, a ceramic, a metal, a resin, a gel and a membrane. Useful types of solid supports include plates, beads, microbeads, whiskers, fibers, combs, hybridization chips, membranes, single crystals, ceramics, and self-assembling monolayers.

Nucleic acids may be attached to the solid support by covalent binding such as by conjugation with a coupling agent or by non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (Sano et al. (1991) *Bio/Technology* 9:1378), or derivatives or combinations of these agents. Nucleic acids may be attached to the solid support by a photocleavable bond, an electrostatic bond, a disulfide bond, a peptide bond, a diester bond or a combination of these bonds. Nucleic acids are also optionally attached to solid supports by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

In addition, nucleic acids are optionally attached to solid supports via spacer moieties between the nucleic acids and the solid support. Useful spacers include a coupling agent, as described above for binding to other or additional coupling partners, or to render the attachment to the solid support cleavable.

Cleavable attachments can be created by attaching cleavable chemical moieties between the nucleic acids and the solid support including, e.g., an oligopeptide, oligonucleotide, oligopolyamide, oligoacrylamide, oligoethylene glycerol, alkyl chains of between about 6 to 20 carbon atoms, and combinations thereof. These moieties may be cleaved with, e.g., added chemical agents, electromagnetic radiation, or enzymes. Exemplary attachments cleavable by enzymes include peptide bonds which can be cleaved by proteases, and phosphodiester bonds which can be cleaved by nucleases.

Chemical agents such as β-mercaptoethanol, dithiothreitol (DTT) and other reducing agents cleave disulfide bonds. Other agents that may be useful include oxidizing agents, hydrating agents and other selectively active compounds. Electromagnetic radiation such as ultraviolet, infrared and visible light cleave photocleavable bonds. Attachments may also be reversible, e.g., using heat or enzymatic treatment, or reversible chemical or magnetic attachments. Release and reattachment can be performed using, e.g., magnetic or electrical fields.

The nucleotide incorporating biocatalysts utilized in the methods described herein typically comprise enzymes, such as polymerases, terminal transferases, reverse transcriptases, telomerases, polynucleotide phosphorylases, and the like. For example, the polymerase optionally lacks an F to Y mutation in helix O of the enzyme or otherwise lacks a mutation that enhances incorporation of 3'-deoxynucleotides by the enzyme. Optionally, the enzyme comprises a 3'-5' exonuclease activity and/or is a thermostable enzyme. The enzyme is typically derived from an organism, such as *Thermus antranikianii*, *Thermus aquaticus*, *Thermus caldophilus*, *Thermus chliarophilus*, *Thermus filiformis*, *Thermus flavus*, *Thermus igniterrae*, *Thermus lacteus*, *Thermus oshimai*, *Thermus ruber*, *Thermus rubens*, *Thermus scotoductus*, *Thermus silvanus*, *Thermus* species Z05, *Thermus* species sps 17, *Thermus thermophilus*, *Thermotoga maritima*, *Thermotoga neapolitana*, *Thermosipho africanus*, *Anaerocellum thermophilum*, *Bacillus caldotenax*, *Bacillus stearothermophilus*, or the like.

In some embodiments, the enzyme is modified. Exemplary modified enzymes include, e.g., a G46E E678G CS5 DNA polymerase, a G46E E678G CS6 DNA polymerase, a Δ ZO5R polymerase, a G46E L329A E678G CS5 DNA polymerase, and the like. The modified enzymes of the invention generally comprise an increased ability to incorporate 2'-terminator nucleotides relative to an unmodified enzyme. To further illustrate, the modified enzymes of the invention typically comprise mutations that enhance incorporation of ribonucleotides, that enhance incorporation of 2'-modified analogs of ribonucleotides, and/or that reduce or eliminate 5'-3' exonuclease activity, e.g., relative to an enzyme that lacks one or more of these mutations. Additional details relating to the nucleotide incorporating biocatalysts useful in practicing the methods of the present invention are provided in, e.g., U.S. Pat. No. 5,939,292, entitled "THERMOSTABLE DNA POLYMERASES HAVING REDUCED DISCRIMINATION AGAINST RIBO-NTPS," which issued Aug. 17, 1999 to Gelfand et al., U.S. Pat. No. 4,889,818, entitled "PURIFIED THERMOSTABLE ENZYME," which issued Dec. 26, 1989 to Gelfand et al., U.S. Pat. No. 5,374,553, entitled "DNA ENCODING A THERMOSTABLE NUCLEIC ACID POLYMERASE ENZYME FROM THERMOTOGA MARITIMA," which issued Dec. 20, 1994 to Gelfand et al., U.S. Pat. No. 5,420,029, entitled "MUTATED THERMOSTABLE NUCLEIC ACID POLYMERASE ENZYME FROM THERMOTOGA MARITIMA," which issued May 30, 1995 to Gelfand et al., U.S. Pat. No. 5,455,170, entitled "MUTATED THERMOSTABLE NUCLEIC ACID POLYMERASE ENZYME FROM THERMUS SPECIES Z05," which issued Oct. 3, 1995 to Abramson et al., U.S. Pat. No. 5,466,591, entitled "5' TO 3' EXONUCLEASE MUTATIONS OF THERMOSTABLE DNA POLYMERASES," which issued Nov. 14, 1995 to Abramson et al., U.S. Pat. No. 5,618,711, entitled "RECOMBINANT EXPRESSION VECTORS AND PURIFICATION METHODS FOR THERMUS THERMOPHILUS DNA POLYMERASE," which issued Apr. 8, 1997 to Gelfand et al., U.S. Pat. No. 5,624,833, entitled "PURIFIED THERMOSTABLE NUCLEIC ACID POLYMERASE ENZYME FROM THERMOTOGA MARITIMA," which issued Apr. 29, 1997 to Gelfand et al., U.S. Pat. No. 5,674,738, entitled "DNA ENCODING THERMOSTABLE NUCLEIC ACID POLYMERASE ENZYME FROM THERMUS SPECIES Z05," which issued Oct. 7, 1997 to Abramson et al., U.S. Pat. No. 5,789,224, entitled "RECOMBINANT EXPRESSION VECTORS AND PURIFICATION METHODS FOR THERMUS THERMOPHILUS DNA POLYMERASE," which issued Aug. 4, 1998 to Gelfand et al., U.S. Pat. No. 5,795,762, entitled "5' TO 3' EXONUCLEASE MUTATIONS OF THERMOSTABLE DNA POLYMERASES," which issued Aug. 18, 1998 to Abramson et al., U.S. Pat. Application Publication No. US 2002/0012970, entitled "HIGH TEMPERATURE REVERSE TRANSCRIPTION USING MUTANT DNA POLYMERASES," which published Jan. 31, 2002 by Smith et al., and U.S. patent application Ser. No. 10/401,403, filed Mar. 26, 2003, which are each incorporated by reference.

The production of modified enzymes with, e.g., enhanced efficiency for incorporating 2'-terminator nucleotides may be accomplished by various processes including, e.g., site-directed mutagenesis. See, for example, Sambrook et al., supra. More specifically, site-directed mutagenesis is generally accomplished by site-specific primer-directed mutagenesis. This technique is typically conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. To further illustrate, many other approaches to modify nucleic acids, such as "recombinant PCR" methods can also be utilized (see, e.g., Innis et al., supra).

Nucleotide incorporating biocatalysts typically produce multiple different extended primer nucleic acids and the methods also generally include resolving the multiple different extended primer nucleic acids such that at least a portion of a base sequence of the template nucleic acid is determinable from the resolved extended primer nucleic acids. For example, the extended primer nucleic acids are optionally resolved by: determining the molecular masses, sizes, and/or charge properties of the extended primer nucleic acids. In certain embodiments, the extended primer nucleic acids further comprise labels and the extended primer nucleic acids are resolved by separating the labeled extended primer nucleic acids from each other and detecting (e.g., spectrophotometrically, etc) detectable signals produced by the labels. To illustrate, the labeled extended primer nucleic acids are separated by at least one separation technique, such as electrophoresis, chromatography, gas phase ion spectrometry, and/or the like.

IV. REACTION MIXTURES

The invention also provides reaction mixtures that comprise at least one labeled 2'-terminator nucleotide as described herein (e.g., a labeled 2'-monophosphate-3'-hydroxyl-5'-triphosphate nucleoside, etc.) and at least one nucleotide incorporating biocatalyst as described herein. In some embodiments, the reaction mixture also includes at least one pyrophosphatase (e.g., a thermostable pyrophosphatase). The reaction mixture optionally further includes one or more extendible nucleotides (e.g., ribonucleotides, deoxyribonucleotides, and/or the like). Optionally, at least one of the extendible nucleotides is labeled. Labeling is described further above. Typically, the 2'-terminator nucleotide and the extendible nucleotides are present in a molar ratio of 1:1 or less. In certain embodiments, the reaction mixture also includes a template nucleic acid and a primer nucleic acid that is at least partially complementary to at least a subsequence of the template nucleic acid. Optionally, the template nucleic acid or the primer nucleic acid is attached (e.g., covalently or noncovalently) to a solid support. In some of these embodiments, the primer comprises a label (e.g., fluorescent dyes, radioisotopes, mass-modifying group, etc.). Solid supports and labels are described in greater detail above.

To further illustrate, but not to limit the present invention, one set of representative reaction conditions for sequencing a template DNA are provided, which are of use in the 2'-terminator nucleotide-related methods described herein. In particular, the 2'-terminator nucleotides referred to in this exemplary set of conditions are 2'-monophosphate-3'-hydroxyl-5'-triphosphate nucleosides (abbreviated as N-tetra-PO$_4$s).

The primer nucleic acid extensions are optionally performed in four separate reactions. Components in common to each of the reactions include:
50 mM Tricine at pH 8.5,
40 mM KOAc,
4 mM Mg(OAc)$_2$,
100 µM each of dATP, dCTP, and dTTP,
150 µM c7dGTP,
20 ng/µl M13 mp 18 DNA template,
0.5 U/µl G46E E678G CS5 DNA polymerase, and
1.0 U/µl rTth Thermostable Pyrophosphatase.

Individual reactions further include, as follows:
A Reaction:
10 µl reaction volume,
0.1 µM FR686N-HEX primer nucleic acid, and
3.5 µM A-tetra-PO$_4$
C Reaction:
10 µl reaction volume,
0.1 µM FR686N-FAM primer nucleic acid, and
7.5 µM C-tetra-PO$_4$
G Reaction:
20 µl reaction volume,
0.1 µM FR686N-TAMRA primer nucleic acid, and
5 µM G-tetra-PO$_4$
U Reaction:
20 µl reaction volume,
0.1 µM FR686N—ROX primer nucleic acid, and
10 µM U-tetra-PO$_4$ Following thermal cycling, the reaction mixtures are optionally combined, ethanol precipitated, and resuspended in formamide. The resuspended sample is then resolved, e.g., by electrophoresis and analyzed on a DNA sequencer (e.g., an ABI 377 DNA sequencer (Applied Biosystems, Foster City, Calif.) or the like).

V. DETECTABLE SIGNAL DETECTION

The extended nucleic acids of the invention can be detected using essentially any detection method. For example, fluorescence is optionally detected by detectors or sensors, such as photomultiplier tubes (PMTs), charge-coupled devices (CCDs), intensified CCDs, photodiodes, avalanche photodiodes, optical sensors, scanning detectors, or the like. Detectors such as these are readily available from various commercial sources including, e.g., Applied Biosystems (Foster City, Calif.). Detection systems of use in practicing the methods of the invention are described further in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), which are incorporated by reference.

In some embodiments of the invention, the method further includes detecting a molecular mass or molecular weight of the extended primer nucleic acid or a fragment thereof. A genotype of the template nucleic acid is typically determinable from the detected molecular mass of the extended primer nucleic acid or the fragment thereof. For example, a specific nucleic acid sequence will typically have a unique or relatively unique molecular weight depending on its size and composition. That molecular weight can be determined, for example, by chromatography (e.g. HPLC), nuclear magnetic resonance (NMR), high-definition gel electrophoresis, capillary electrophoresis (e.g. HPCE), spectroscopy, or gas phase ion spectrometry (e.g., mass spectrometry, etc.). Typically, molecular weights are determined by measuring the mass/charge ratio with mass spectrometry.

Mass spectrometry of biopolymers such as nucleic acids can be performed using a variety of techniques (e.g. U.S. Pat. Nos. 4,442,354; 4,931,639; 5,002,868; 5,130,538; 5,135,870; 5,174,962). Difficulties associated with volatilization of high molecular weight molecules such as DNA and RNA have been overcome, at least in part, with advances in techniques, procedures and electronic design. Further, only small quantities of sample are needed for analysis, the typical sample being a mixture of 10 or so fragments. Quantities which range from between about 0.1 femtomole to about 1.0 nanomole, preferably between about 1.0 femtomole to about 1000 femtomoles and more preferably between about 10 femtomoles to about 100 femtomoles are typically sufficient for analysis. These amounts can be easily placed onto the individual positions of a suitable surface or attached to a support.

Exemplary techniques that can be used to volatize a nucleic acid include fast atom bombardment, plasma desorption, matrix-assisted laser desorption/ionization, electrospray, photochemical release, electrical release, droplet release, resonance ionization, and combinations of these techniques.

In electrohydrodynamic ionization, thermospray, aerospray and electrospray, the nucleic acid is dissolved in a solvent and injected with the help of heat, air or electricity, directly into the ionization chamber. If the method of ionization involves a light beam, particle beam or electric discharge, the sample may be attached to a surface and introduced into the ionization chamber. In such situations, a plurality of samples may be attached to a single surface or multiple surfaces and introduced simultaneously into the ionization chamber and still analyzed individually. The appropriate sector of the surface which contains the desired nucleic acid can be moved proximate to the path of an ionizing beam. After the beam is pulsed on and the surface bound molecules are ionized, a different sector of the surface is moved into the path of the beam and a second sample, with the same or different molecule, is analyzed without reloading the machine. Multiple samples may also be introduced at electrically isolated regions of a surface. Different sectors of a solid support, such as a chip are typically connected to an electrical source and ionized individually. The surface to which the sample is attached may be shaped for maximum efficiency of the ionization method used. For field ionization and field desorption, a pin or sharp edge is an efficient solid support and for particle bombardment and laser ionization, a flat surface.

An objective of ionization for mass spectrometry is to produce a whole molecule with a charge. Optionally, a matrix-assisted laser desorption/ionization (MALDI) (see, e.g., Sauer et al. (2002) "Facile method for automated genotyping of single nucleotide polymorphisms by mass spectrometry," *Nucleic Acids Res.* 30(5):e22, which is incorporated by reference) or electrospray (ES) mass spectroscopy is used to determine molecular weight and, thus, sequence information for the template nucleic acids. It will be recognized by those of ordinary skill that a variety of methods may be used which are appropriate for large molecules such as nucleic acids. Typically, a nucleic acid is dissolved in a solvent and injected into the ionization chamber, using electrohydrodynamic ionization, thermospray, aerospray or electrospray. Nucleic acids may also be attached to a surface and ionized with a beam of particles or light. Particles that have been successfully used include plasma (plasma desorption), ions (fast ion bombardment) or atoms (fast atom bombardment). Ions have also been produced with the rapid application of laser energy (laser desorption) and electrical energy (field desorption).

In mass spectrometer analysis, the sample is ionized briefly by a pulse of laser beams or by an electric field induced spray. The ions are accelerated in an electric field and sent at a high velocity into the analyzer portion of the spectrometer. The speed of the accelerated ion is directly proportional to the charge (z) and inversely proportional to the mass (in) of the ion. The mass of the molecule may be deduced from the flight characteristics of its ion. For small ions, the typical detector has a magnetic field, which functions to constrain the ions stream into a circular path. The radii of the paths of equally charged particles in a uniform magnetic field are directly proportional to mass. That is, a heavier particle with the same charge as a lighter particle will have a larger flight radius in a magnetic field. It is generally considered to be impractical to measure the flight characteristics of large ions such as nucleic acids in a magnetic field because the relatively high mass to charge (m/z) ratio requires a magnet of unusual size or strength. To overcome this limitation the electrospray method, for example, can consistently place multiple ions on a molecule. Multiple charges on a nucleic acid will decrease the mass to charge ratio allowing a conventional quadrupole analyzer to detect species of up to 100,000 daltons.

Nucleic acid ions generated by the matrix assisted laser desorption/ionization only have a unit charge and because of their large mass, generally utilize analysis by a time-of-flight (TOP) mass analyzer. Time of flight analyzers are typically long tubes with a detector at one end. In the operation of a TOF analyzer, a sample is ionized briefly and accelerated down the tube. After detection, the time needed for travel down the detector tube is calculated. The mass of the ion may be calculated from the time of flight. TOP mass analyzers do not typically utilize a magnetic field and can detect unit charged ions with a mass of up to 100,000 daltons. For improved resolution, the time of flight mass spectrometer may include a reflectron, a region at the end of the flight tube, which negatively accelerates ions. Moving particles entering the reflectron region, which contains a field of opposite polarity to the accelerating field, are retarded to zero speed and then reverse accelerated out with the same speed but in the opposite direction. In the use of a mass analyzer with a reflectron, the detector is placed on the same side of the flight tube as the ion source to detect the returned ions and the effective length of the flight tube and the resolution power is effectively doubled. The calculation of mass to charge ratio from the time of flight data takes into account of the time spent in the reflectron.

Ions with the same charge to mass ratio will typically leave the ion accelerators with a range of energies because the ionization regions of a mass spectrometer are not a point source. Ions generated further away from the flight tube, spend a longer time in the accelerator field and enter the flight tube at a higher speed. Thus, ions of a single species of molecule will arrive at the detector at different times. In time of flight mass analysis, a longer time in the flight tube in theory provide more sensitivity, but due to the different speeds of the ions, the noise (background) will also be increased. A reflectron, besides effectively doubling the effective length of the flight tube, can reduce the error and increase sensitivity by reducing the spread of detector impingement time of a single species of ions. An ion with a higher velocity will enter the reflectron at a higher velocity and stay in the reflectron region longer than a lower velocity ion. If the reflectron electrode voltages are arranged appropriately, the peak width contribution from the initial velocity distribution can be largely corrected for at the plane of the detector. The correction provided by the reflectron leads to increased mass resolution of all stable ions (i.e., those that do not dissociate in flight) in the spectrum.

While a linear field reflectron functions adequately to reduce noise and enhance sensitivity, reflectrons with more complex field strengths offer superior correctional abilities and a number of complex reflectrons can be used. The double stage reflectron has a first region with a weaker electric field and a second region with a stronger electric field. The quadratic and the curve field reflectron have a electric field which increases as a function of the distance. These functions, as their name implies, may be a quadratic or a complex exponential function. The dual stage, quadratic, and curve field reflectrons, while more elaborate are also more accurate than the linear reflectron.

The detection of ions in a mass spectrometer is typically performed using electron detectors. To be detected, the high mass ions produced by the mass spectrometer are converted into either electrons or low mass ions at a conversion electrode. These electrons or low mass ions are then used to start the electron multiplication cascade in an electron multiplier and further amplified with a fast linear amplifier. The signals from multiple analysis of a single sample are combined to improve the signal to noise ratio and the peak shapes, which also increase the accuracy of the mass determination.

Multiple primary ions can be detected directly through the use of ion cyclotron resonance and Fourier analysis. This is useful for the analysis of a complete sequencing ladder immobilized on a surface. In this method, a plurality of samples is ionized at once and the ions are captured in a cell with a high magnetic field. An RF field excites the population of ions into cyclotron orbits. Because the frequencies of the orbits are a function of mass, an output signal representing the spectrum of the ion masses is obtained. This output is analyzed by a computer using Fourier analysis, which reduces the combined signal to its component frequencies and thus provides a measurement of the ion masses present in the ion sample. Ion cyclotron resonance and Fourier analysis can determine the masses of all nucleic acids in a sample. The application of this method is especially useful on a sequencing ladder.

The data from mass spectrometry, either performed singly or in parallel (multiplexed), can determine the molecular mass of a nucleic acid sample. The molecular mass, combined with the known sequence of the sample, can be analyzed to determine the length of the sequence. Because different bases have different molecular weight, the output of a high resolution mass spectrometer, combined with the known sequence and reaction history of the sample, will determine the sequence and length of the nucleic acid analyzed. In the mass spectroscopy of a sequencing ladder, generally the base sequence of the primers is known. From a known sequence of a certain length, the added base of a sequence one base longer can be deduced by a comparison of the mass of the two molecules. This process is continued until the complete sequence of a sequencing ladder is determined.

VI. SYSTEMS

In another aspect, the invention relates to a system for extending a nucleic acid. The system includes (a) at least one container comprising a labeled 2'-terminator nucleotide. Typically, the system comprises a plurality of containers, e.g., for performing multiple extension reactions in parallel. The system also includes (b) at least one thermal modulator (e.g., a thermocycling device, etc.) operably connected to the container to modulate temperature in the container, and/or (c) at least one fluid transfer component (e.g., an automated pipettor, etc.) that transfers fluid to and/or from the container. Thermocycling devices, some of which are embodied in microfluidic devices, and various fluid transfer devices suitable or adaptable for use in the systems of the invention are generally known in the art. The system optionally further includes at least one detector operably connected to the container to detect detectable signals produced in the container. The system typically further includes at least one controller operably connected to the thermal modulator to effect modulation of the temperature in the container and/or to the fluid transfer component to effect transfer of the fluid to and/or from the container.

The systems of the invention include various embodiments. For example, detection components that are structured to detect detectable signals produced, e.g., in or proximal to another component of the system (e.g., in reaction container, etc.). Suitable signal detectors that are optionally utilized, or adapted for use, in these systems detect, e.g., fluorescence, phosphorescence, radioactivity, mass, concentration, pH, charge, absorbance, refractive index, luminescence, temperature, magnetism, or the like. Detectors optionally monitor one or a plurality of signals from upstream and/or downstream of the performance of, e.g., a given assay step. For example, the detector optionally monitors a plurality of optical signals, which correspond in position to "real time" results. Example detectors or sensors include photomultiplier tubes, CCD arrays, optical sensors, temperature sensors, pressure sensors, pH sensors, conductivity sensors, scanning detectors, or the like. Each of these as well as other types of sensors is optionally readily incorporated into the systems described herein. Optionally, the systems of the present invention include multiple detectors.

Essentially any analytic component can be utilized or adapted for use in the systems of the invention. Certain exemplary analytic components that are optionally utilized in these systems include, e.g., a liquid chromatography column, a gel electrophoresis column, a electrochromatography column, a resonance light scattering detector, an emission spectroscope, a fluorescence spectroscope, a phosphorescence spectroscope, a luminescence spectroscope, a spectrophotometer, a photometer, a calorimeter, a mass spectrometer, a nuclear magnetic resonance spectrometer, an electron paramagnetic resonance spectrometer, an electron spin resonance spectroscope, a turbidimeter, a nephelometer, a Raman spectroscope, a refractometer, an interferometer, an x-ray diffraction analyzer, an electron diffraction analyzer, a polarimeter, an optical rotary dispersion analyzer, a circular dichroism spectrometer, a potentiometer, a chronopotentiometer, a coulometer, an amperometer, a conductometer, a gravimeter, a thermal gravimeter, a titrimeter, a differential scanning colorimeter, a radioactive activation analyzer, a radioactive isotopic dilution analyzer, or the like. Various synthetic components are also utilized, or adapted for, use in the systems of the invention including, e.g., automated nucleic acid synthesizers. Analytic and synthetic components that are optionally included in the systems of the invention are described further in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), which are incorporated by reference.

The systems of the invention also typically include controllers that are operably connected to one or more components (e.g., analytic components, synthetic components, thermal modulator, fluid transfer components, detectors, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

To illustrate, some embodiments of the invention provide computers and/or computer readable media comprising data sets that comprise at least one character corresponding to at least one 2'-terminator nucleotide as described herein. Typically, the data sets comprise a plurality of character strings corresponding to a plurality of nucleic acid sequences.

The computer can be, e.g., a PC (Intel x86 or Pentium chip-compatible DOS™, OS2™, WINDOWS™, WINDOWS NT™, WINDOWS95™, WINDOWS98™, WINDOWS2000™, WINDOWS XP", LINUX-based machine, a MACINTOSH™, Power PC, or a UNIX-based (e.g., SUN™ work station) machine) or other common commercially available computer which is known to one of skill: Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., controlling temperature modulators and fluid flow regulators is optionally constructed by one of skill using a standard programming language such as Visual basic, Fortran, Basic, Java, or the like.

VII. KITS

The present invention also provides kits for extending nucleic acids. The kits include (a) at least one nucleotide incorporating biocatalyst as described herein, and (b) at least one labeled 2'-terminator nucleotide as described herein. For example, the 2'-terminator nucleotide optionally includes at least one label (e.g., a radioisotope, a fluorescent dye, a mass-modifying group, or the like). In some embodiments, the kit further includes one or more extendible nucleotides and optionally, at least one of the extendible nucleotides comprises a label (e.g., a radioisotope, a fluorescent dye, a mass-modifying group, or the like). Optionally, the kit further includes at least one pyrophosphatase (e.g., a thermostable pyrophosphatase, etc.). Typically, the kit also includes (c) a set of instructions for extending the nucleic acid with the nucleotide incorporating biocatalyst and the 2'-terminator nucleotide. Further, the kit optionally also includes (d) at least one container for packaging the nucleotide incorporating biocatalyst, the labeled 2'-terminator nucleotide, and the set of instructions. In certain embodiments, the kit further includes a template nucleic acid and the primer nucleic acid, which primer nucleic acid is complementary to at least a subsequence of the template nucleic acid. Optionally, the template nucleic acid or the primer nucleic acid is attached to a solid support, e.g., as described herein. In some of these embodiments, the primer comprises a label, such as a radioisotope, a fluorescent dye, a mass-modifying group, or the like.

VIII. EXAMPLE 1

Automated Cycle DNA Sequencing Using a Modified Thermostable DNA Polymerase and Fluorescent Primers This example illustrates the application of the 2'-terminator nucleotides of the invention to automated dye primer cycle DNA sequencing. In particular, an M13 mp 18 DNA template was sequenced using ribonucleoside 2'-monophosphate 5'-triphosphates.

Cycle sequencing reactions were performed with G46E E678G CS5 DNA polymerase (referred to above) modified for the incorporation of ribonucleotide analogs, dye primers, and ribonucleoside 2'-monophosphate 5'-triphosphate analogs. Reactions consisted of 50 mM Tricine pH 8.5; 40 mM KOAc; 4 mM Mg(OAc)$_2$; 100 µM each dATP, dCTP, dTTP; 150 µM c7dGTP; 0.5 unit/µl G46E E678G CS5 DNA polymerase; 1.0 unit/µl rTth Thermostable Pyrophosphatase; and 20 ng/µl M13 mp 18 template. Four individual reactions, one for each base were performed. Reactions for each of the bases contained the above plus the following reagents:

Adenosine reactions (10 µl):
3.5 µM Adenosine 2'-monophosphate 5'-triphosphate
0.1 µM FR686NHEX primer
Cytidine reactions (10 µl):
7.5 µM Cytidine 2'-monophosphate 5'-triphosphate
0.1 µM FR686NFAM primer
Guanosine reactions (20 µl):
5 µM Guanosine 2'-monophosphate 5'-triphosphate
0.1 µM FR686NTAMRA primer
Uridine reactions (20 µl):
10 µM Uridine 2'-monophosphate 5'-triphosphate
0.1 µM FR686NROX primer In the adenosine reactions, the adenosine 2'-monophosphate 5'-triphosphate was approximately 95% pure (i.e., about 5% was the adenosine 3'-monophosphate 5'-triphosphate). In the cytidine reactions, the cytidine 2'-monophosphate 5'-triphosphate and the cytidine 3'-monophosphate 5'-triphosphate were present as 50/50 mixture. In the guanosine reactions, the guanosine 2'-monophosphate 5'-triphosphate was approximately 94% pure (i.e., about 6% was the guanosine 3'-monophosphate 5'-triphosphate). In the uridine reactions, the uridine 2'-monophosphate 5'-triphosphate was 100% pure.

The oligonucleotide primer sequences were, as follows:

| | |
|---|---|
| FR686N | CGCCAGGGTTTTCCCAGTEA (SEQ ID NO: 1) E = 2'-amino (ribo) C |
| FR686NFAM | Dye = 5' FAM ABD |
| FR686NHEX | Dye = 5' HEX ABD |

| | |
|---|---|
| FR686NROX | Dye = 6-ROX |
| FR686NTAMRA | Dye = C6-amino TAMRA |

Each of the four reactions were placed in a Perkin-Elmer GeneAmp® PCR system 9600 thermal cycler and subjected to 95° C. for 45 seconds and then 20 cycles of 95° C. for 15 seconds, 55° C. for 15 seconds, 70° C. for 90 seconds, followed by 20 cycles of 95° C. for 15 seconds, 70° C. for 90 seconds. The four reactions were pooled and precipitated by the addition of 144 μl 100% ethanol and 6 μl 3M NaOAc (pH 5.2) at 4° C. for 15 minutes. The pooled reactions were microcentrifuged at 4° C. for 15 minutes to precipitate the DNA, and the supernatant was removed. The pellet was washed with 350 μl cold 70% ethanol, microcentrifuged at 4° C. for 5 minutes, supernatant removed, and the DNA pellet dried. The precipitated DNA was resuspended in 10 μl Hi-Di formamide (Applied Biosystems, Foster City, Calif., part #4311320), heated at 90° C. for 3 minutes and placed on ice. 2 μl of each sample was loaded onto a pre-electrophoresed 48 cm 4.25% acrylamide:bis (29:1), 6 M urea gel and electrophoresed for 7 hours on an ABI PRISM™ 377 DNA Sequencer (Applied Biosystems, Foster City, Calif.).

Figure 7:
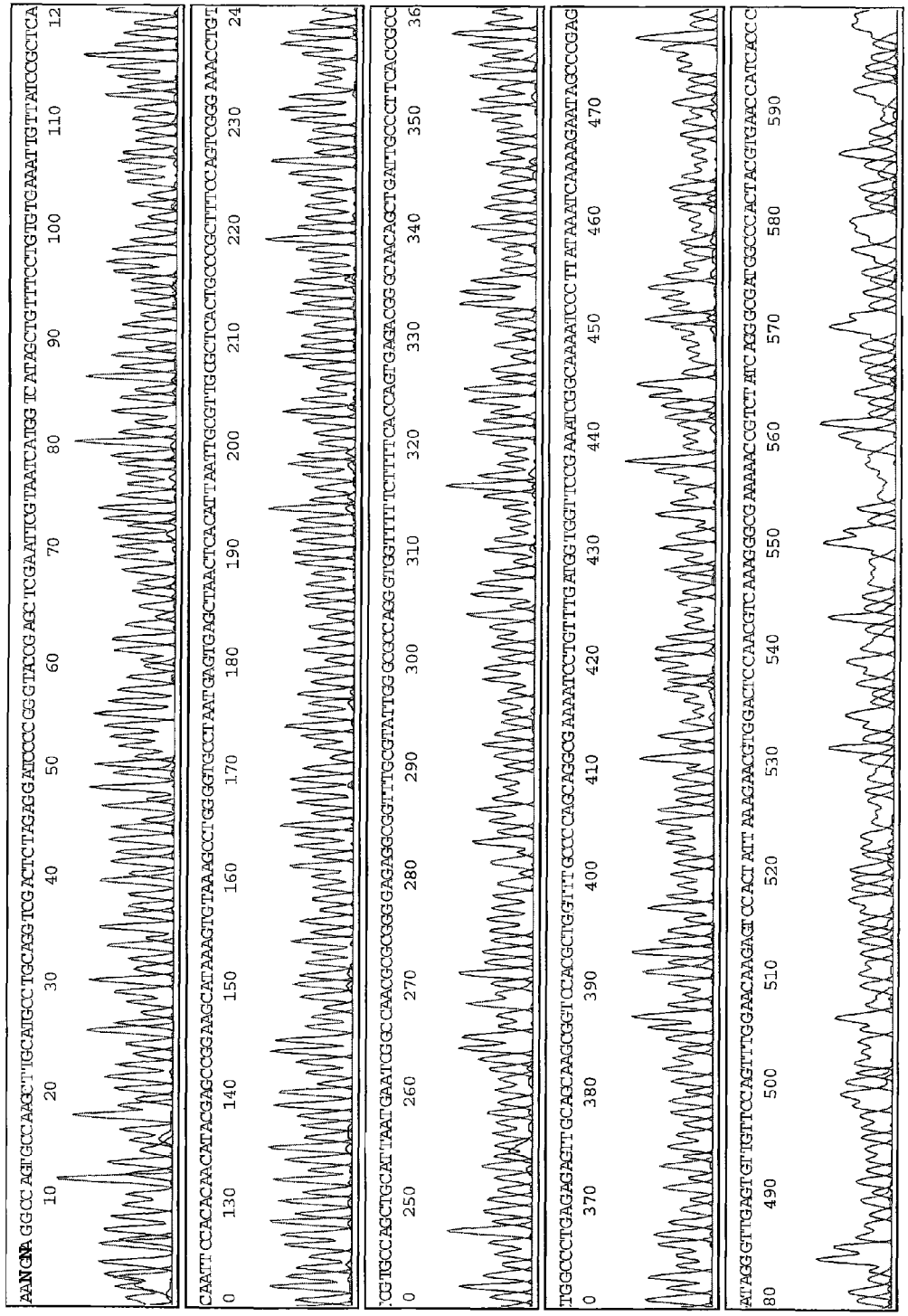
FIG. 7 is a spectral profile that shows the data from a sequence analysis of an M13 mp 18 DNA template using unlabeled 2'-terminator nucleotides and a fluorescent dye-labeled primer.

Data was analyzed with Sequencing Analysis Software 3.4.1 (Applied Biosystems, Foster City, Calif.) using primer file DP4% Ac{KS}, the semiadaptive basecaller version 3.3.1b2, and a matrix file specific for the dye primers used above generated following the procedure in the Applied Biosystems manual (part #903436). Automated basecalling by the analysis software was 100% accurate for bases +18 to +739 from the sequencing primer when compared to an M13 mp18 reference sequence. FIG. 7 provides a spectral profile of the data from this sequence analysis.

IX. EXAMPLE 2

Cycled DNA Primer Extension Using a Modified Thermostable DNA Polymerase and Dye-Labeled Ribonucleoside 2'-Monophosphate 5'-Triphosphate A thermal cycled primer extension reaction was performed with G46E E678G CS5 DNA polymerase modified for the incorporation of ribonucleotide analogs, unlabeled primer, and TAMRA dye-labeled uridine 2'-monophosphate 5'-triphosphate. The 20 μl reaction consisted of 50 mM Tricine pH 7.5; 25 mM KOAc; 2.5 mM Mg(OAc)$_2$; 100 μM each dATP, dCTP, and dTTP; 150 μM dITP; 0.5 unit/μl G46E E678G CS5 DNA polymerase; 1.0 unit/μl rTth Thermostable inorganic pyrophosphatase; 5 ng/μl M13 mp18 template; 0.15 μM primer; and 0.25 μM TAMRA-uridine 2'-phosphate 5'-triphosphate.

A control reaction was performed with AmpliTaq DNA polymerase, FS, unlabeled primer and TAMRA dye-labeled ddTTP. The 20 μl reaction consisted of 50 mM Tris pH 9; 2 mM MgCl$_2$; 100 μM each dATP, dCTP, and dTTP; 150 μM dITP; 0.5 unit/μl AmpliTaq DNA polymerase, FS; 1.0 unit/μl rTth Thermostable inorganic pyrophosphatase; 5 ng/μM13mp18 template; 0.15 μM FR686N primer; and 0.2 μM TAMRA-ddTTP.

The reactions were placed in a Perkin-Elmer GeneAmp® PCR system 9700 thermal cycler and subjected to 96° C. for 20 seconds and then 25 cycles of 96° C. for 10 seconds, 50° C. for 5 seconds, 60° C. for 4 minutes. After cycling unincorporated dye-labeled terminator was removed from the reaction by centrifugation at 700×g for two minutes through a Sephadex-G50 column (Sigma, Part No G-50-80). The sample was heated at 95° C. for 3 minutes and placed on ice. The samples were electrophoresed on an Applied Biosystems 3100 Genetic Analyzer with the GeneScan application following the StdSeq50_POP6DefaultModule parameters using a 50 cm capillary array and POP6 polymer.

Figure 8:
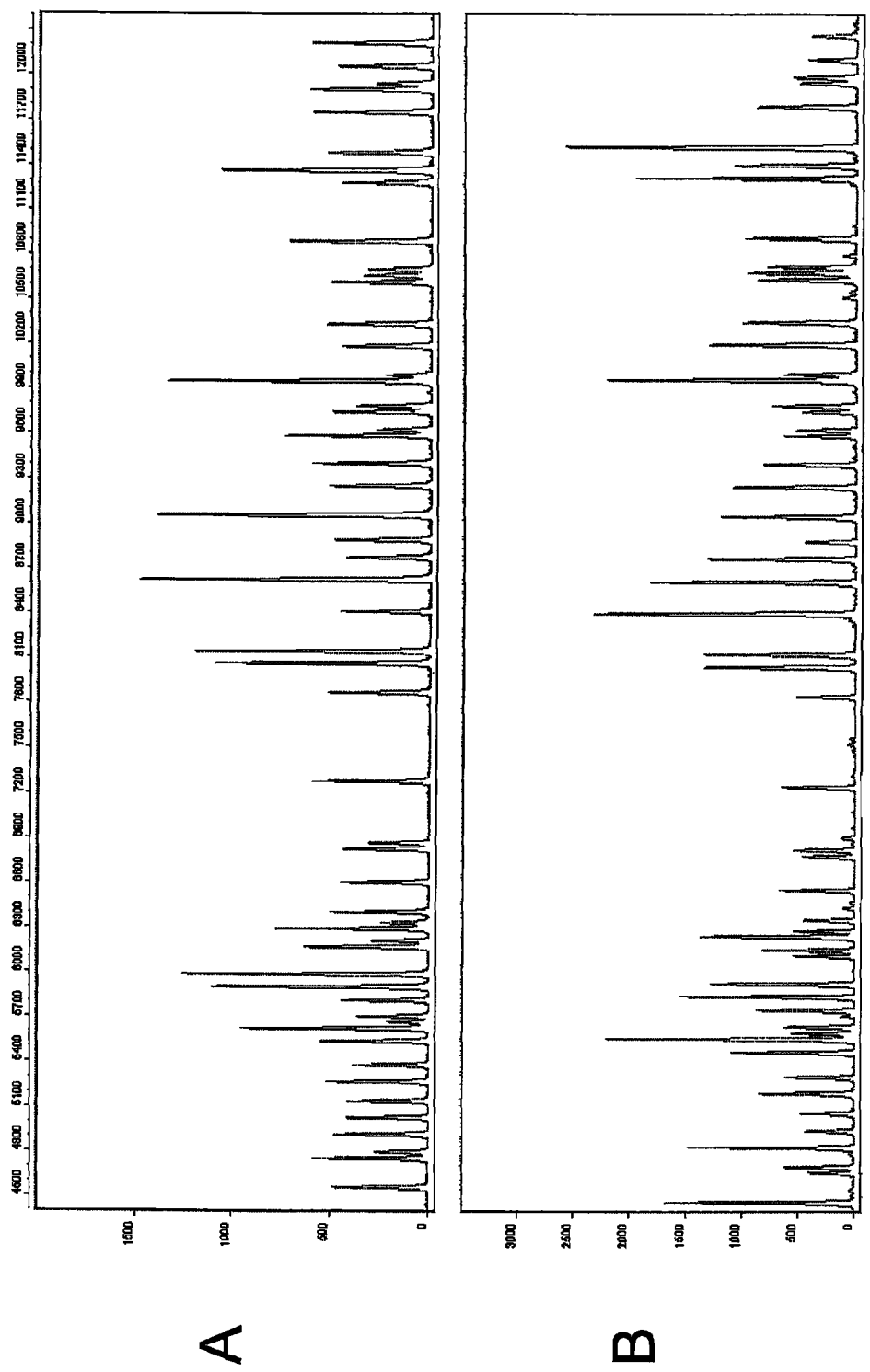
FIGS. 8 A and B are spectral profiles that show the data from a sequence analysis of an M13 mp 18 DNA template using an unlabeled primer and a fluorescent dye-labeled 2'-terminator nucleotide.

Data was analyzed with Applied Biosystems GeneScan 3.7 fragment analysis software. FIG. 8 shows the fragment pattern for T peaks 77 to 273 bases from primer FR686N. More specifically, comparison of the fragment pattern generated with G46E E678G CS5 DNA polymerase and TAMRA-uridine 2'-monophosphate 5'-triphosphate (panel B) to the fragment pattern generated with the control AmpliTaq DNA Polymerase, FS and TAMRA-ddTTP (panel A) revealed a similar pattern of peaks.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of extending a primer nucleic acid, the method comprising: incubating a template nucleic acid with at least one nucleotide incorporating biocatalyst, at least one 2'-terminator nucleotide, and at least one primer nucleic acid that is at least partially complementary to at least a subsequence of the template nucleic acid, which primer nucleic acid comprises DNA, under conditions whereby the nucleotide incorporating biocatalyst extends the primer nucleic acid to produce at least one extended primer nucleic acid by incorporating the 2'-terminator nucleotide at a terminal end of the extended primer nucleic acid, wherein the 2'-terminator nucleotide comprises the formula:

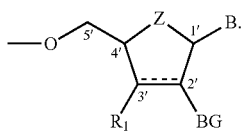

wherein
$R_1$ is H, OH, a hydrophilic group, or a hydrophobic group;
B is at least one homocyclic ring, at least one heterocyclic ring, at least one aryl group, or combinations thereof;
BG is a blocking group; and
Z is O or $CH_2$; and ---- represents a single or double bond,
wherein BG comprises the formula:

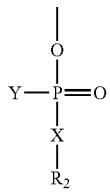

wherein
X is O, S, $NR_3$, $CR_3R_4$ or $SiR_3R_4$;
Y is $CR_5R_6R_7$, $SiR_5R_6R_7$, $OR_5$, $SR_5$, or $NHR_5$;
$R_2$ is H, OH, $NHR_8$, $SR_8$, an alkyl group, a benzyl group, an aryl group, an alkenyl group, an alkynyl group, an alkoxy group, or combinations thereof; and
$R_3$, $R_4$, $R_5$, $R_6$, $R_7$, and $R_8$ are independently selected from H, an alkyl group, a benzyl group, an aryl group, an alkenyl group, an alkynyl group, or combinations thereof; or

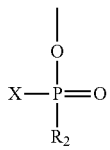

wherein
X is $CR_3R_4R_5$, $SiR_3R_4R_5$, $OR_3$, $SR_3$, or $NHR_3$;
$R_2$ is H, OH, $NHR_6$, $SR_6$, an alkyl group, a benzyl group, an aryl group, an alkenyl group, an alkynyl group, an alkoxy group, or combinations thereof; and,
$R_3$, $R_4$, $R_5$, and $R_6$ are independently selected from H, an alkyl group, a benzyl group, an aryl group, an alkenyl group, an alkynyl group, or combinations thereof.

2. The method of claim 1, wherein the 2'-terminator nucleotide comprises a 2'-monophosphate-3'-hydroxyl-5'-triphosphate nucleoside or a negatively charged blocking group.

3. The method of claim 1, wherein the nucleotide incorporating biocatalyst comprises an enzyme selected from the group consisting of: a polymerase, a terminal transferase, a reverse transcriptase, a polynucleotide phosphorylase, and a telomerase.

4. The method of claim 1, further comprising detecting all or a portion of the extended primer nucleic acid or a fragment thereof.

5. The method of claim 1, wherein at least one of the 2'-terminator nucleotide, the extended primer nucleic acid, and the primer nucleic acid comprises at least one label.

6. The method of claim 5, wherein the label comprises a fluorescent dye, a weakly fluorescent label, a non-fluorescent label, a colorimetric label, a chemiluminescent label, a bioluminescent label, a radioisotope, an antibody, an antigen, biotin, a hapten, or an enzyme.

7. The method of claim 1, wherein the template nucleic acid or the primer nucleic acid is attached to a solid support.

8. The method of claim 1, further comprising incubating the template nucleic acid with at least one extendible nucleotide.

9. The method of claim 8, comprising incubating the template nucleic acid with at least one pyrophosphatase that minimizes pyrophosphorolysis.

10. The method of claim 8, wherein the 2'-terminator nucleotides and the extendible nucleotides are present in a molar ratio of 1:1 or less.

11. The method of claim 8, wherein the nucleotide incorporating biocatalyst produces multiple different extended primer nucleic acids and the method comprises resolving the multiple different extended primer nucleic acids, whereby at least a portion of a base sequence of the template nucleic acid is determinable from the resolved extended primer nucleic acids.

12. The method of claim 11, wherein the extended primer nucleic acids are resolved by determining at least one of the molecular masses, sizes, and charge properties of the extended primer nucleic acids.

13. The method of claim 11, wherein the extended primer nucleic acids further comprise labels and the extended primer nucleic acids are resolved by separating the labeled extended primer nucleic acids from each other and detecting detectable signals produced by the labels.

14. A method of extending a nucleic acid, the method comprising: incubating at least one nucleic acid with at least one nucleotide incorporating biocatalyst and at least one labeled 2'-terminator nucleotide, whereby the nucleotide incorporating biocatalyst extends the nucleic acid to produce at least one extended nucleic acid by incorporating the labeled 2'-terminator nucleotide at a terminal end of the nucleic acid, wherein the labeled 2'-terminator nucleotide comprises the formula:

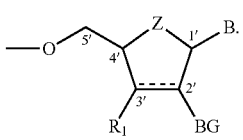

wherein
$R_1$ is H, OH, a hydrophilic group, or a hydrophobic group;
B is at least one homocyclic ring, at least one heterocyclic ring, at least one aryl group, or combinations thereof;
BG is a blocking group; and
Z is O or $CH_2$; and ---- represents a single or double bond, wherein BG comprises the formula:

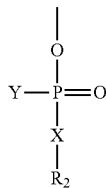

wherein

X is O, S, NR$_3$, CR$_3$R$_4$, or SiR$_3$R$_4$;

Y is CR$_5$R$_6$R$_7$, SiR$_5$R$_6$R$_7$, OR$_5$ SR$_5$, or NHR$_5$; R$_2$ is H, OH, NHR$_8$, SR$_8$, an alkyl group, a benzyl group, an aryl group, an alkenyl group, an alkynyl group, an alkoxy group, or combinations thereof; and, R$_3$, R$_4$, R$_5$, R$_6$, R$_7$, and R$_8$ are independently selected from H, an alkyl group, a benzyl group, an aryl group, an alkenyl group, an alkynyl group, or combinations thereof; or

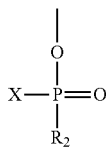

wherein

X is CR$_3$R$_4$R$_5$, SiR$_3$R$_4$R$_5$, OR$_3$, SR$_3$, or NHR$_3$; R$_2$ is H, OH, NHR$_6$, SR$_6$, an alkyl group, a benzyl group, an aryl group, an alkenyl group, an alkynyl group, an alkoxy group, or combinations thereof; and R$_3$, R$_4$, R$_5$, and R$_6$ are independently selected from H, an alkyl group, a benzyl group, an aryl group, an alkenyl group, an alkynyl group, or combinations thereof.

15. The method of claim 14, wherein the nucleotide incorporating biocatalyst comprises an enzyme selected from the group consisting of: a terminal transferase and a polynucleotide phosphorylase.

16. The method of claim 14, wherein the labeled 2'-terminator nucleotide comprises a 2'-monophosphate-3'-hydroxyl-5'-triphosphate nucleoside.

17. The method of claim 14, further comprising hybridizing the extended nucleic acid with another nucleic acid and detecting a detectable signal produced by the label.

18. A method of sequencing a target nucleic acid, the method comprising:
(a) incubating at least one target nucleic acid with one or more polymerases, one or more 2'-terminator nucleotides, one or more extendible nucleotides, and one or more primer nucleic acids that are complementary to at least a subsequence of the target nucleic acid, whereby the polymerases extend the primer nucleic acids to produce primer extension products that incorporate the 2'-terminator nucleotides at 3'-terminal ends of the primer extension products; and,
(b) identifying the 2'-terminator nucleotides in the primer extension products, whereby at least a portion of a base sequence of the target nucleic acid is determinable from the identified 2'-terminator nucleotides
wherein the 2'-terminator nucleotide comprises the formula:

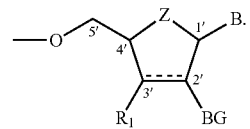

wherein

R$_1$ is H, OH, a hydrophilic group, or a hydrophobic group;

B is at least one homocyclic ring, at least one heterocyclic ring, at least one aryl group, or combinations thereof;

BG is a blocking group; and

Z is O or CH$_2$; and ---- represents a single or double bond, wherein BG comprises the formula:

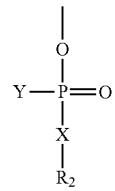

wherein

X is O, S, NR$_3$, CR$_3$R$_4$, or SiR$_3$R$_4$;

Y is CR$_5$R$_6$R$_7$, SiR$_5$R$_6$R$_7$, OR$_5$, SR$_5$, or NHR$_5$;

R$_2$ is H, OH, NHR$_8$, SR$_8$, an alkyl group, a benzyl group, an aryl group, an alkenyl group, an alkynyl group, an alkoxy group, or combinations thereof; and R$_3$, R$_4$, R$_5$, R$_6$, R$_7$, and R$_8$ are independently selected from H, an alkyl group, a benzyl group, an aryl group, an alkenyl group, an alkynyl group, or combinations thereof; or

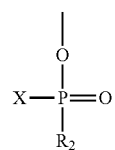

wherein

X is CR$_3$R$_4$R$_5$, SiR$_3$R$_4$R$_5$, OR$_3$, SR$_3$, or NHR$_3$;

R$_2$ is H, OH, NHR$_6$, SR$_6$, an alkyl group, a benzyl group, an aryl group, an alkenyl group, an alkynyl group, an alkoxy group, or combinations thereof; and R$_3$, R$_4$, R$_5$, and R$_6$ are independently selected from H, an alkyl group, a benzyl group, an aryl group, an alkenyl group, an alkynyl group, or combinations thereof.

19. The method of claim 18, wherein (a) comprises incubating the target nucleic acid, the polymerases, the extendible nucleotides, and the primer nucleic acids with at least two different 2'-terminator nucleotides.

20. The method of claim 18, wherein (a) comprises multiple separate reactions, wherein at least two of the reactions comprise different 2'-terminator nucleotides.

21. The method of claim 20, wherein the different 2'-terminator nucleotides comprise different labels.

22. The method of claim 18, wherein (b) comprises determining the molecular masses of the primer extension products or 3'-terminal fragments thereof and the sequence of the target nucleic acid from the molecular masses.

23. The method of claim 18, wherein the primer extension products comprise labels and (b) comprises separating the primer extension products from each other and detecting detectable signals produced by the labels.

24. The method of claim 23, wherein the primer extension products are separated by one or more separation techniques selected from the group consisting of electrophoresis, chromatography, and gas phase ion spectrometry.

* * * * *